United States Patent
Yokota et al.

(10) Patent No.: US 10,190,117 B2
(45) Date of Patent: Jan. 29, 2019

(54) DOUBLE-STRANDED ANTISENSE NUCLEIC ACID WITH EXON-SKIPPING EFFECT

(71) Applicants: National University Corporation Tokyo Medical and Dental University, Tokyo (JP); Osaka University, Suita-shi, Osaka (JP)

(72) Inventors: Takanori Yokota, Tokyo (JP); Kazutaka Nishina, Tokyo (JP); Kotaro Yoshioka, Tokyo (JP); Satoshi Obika, Suita (JP); Takenori Shimo, Suita (JP)

(73) Assignees: National University Corporation Tokyo Medical and Dental University, Tokyo (JP); Osaka University, Osaka (JP)

( * ) Notice: Subject to any disclaimer, the term of this patent is extended or adjusted under 35 U.S.C. 154(b) by 0 days.

(21) Appl. No.: 14/898,630

(22) PCT Filed: Jun. 16, 2014

(86) PCT No.: PCT/JP2014/003208
§ 371 (c)(1),
(2) Date: Dec. 15, 2015

(87) PCT Pub. No.: WO2014/203518
PCT Pub. Date: Dec. 24, 2014

(65) Prior Publication Data
US 2016/0130583 A1    May 12, 2016

Related U.S. Application Data

(60) Provisional application No. 61/836,672, filed on Jun. 19, 2013, provisional application No. 61/835,634, filed on Jun. 16, 2013.

(51) Int. Cl.
| | | |
|---|---|---|
| *C12N 15/113* | (2010.01) | |
| *A61K 31/712* | (2006.01) | |
| *A61K 31/7125* | (2006.01) | |
| *A61K 31/713* | (2006.01) | |

(52) U.S. Cl.
CPC .......... *C12N 15/113* (2013.01); *A61K 31/713* (2013.01); *C12N 2310/11* (2013.01); *C12N 2310/315* (2013.01); *C12N 2310/3231* (2013.01); *C12N 2310/341* (2013.01); *C12N 2310/351* (2013.01); *C12N 2310/3513* (2013.01); *C12N 2310/533* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 6,043,060 A | 3/2000 | Imanishi | |
| 2001/0024808 A1* | 9/2001 | White | C07K 14/47 435/69.1 |
| 2001/0034332 A1* | 10/2001 | Jin | C12Q 1/6809 514/44 R |
| 2001/0039331 A1* | 11/2001 | Hunter | C12N 9/16 530/350 |
| 2002/0068708 A1 | 6/2002 | Wengel et al. | |
| 2003/0105309 A1 | 6/2003 | Imanishi et al. | |
| 2007/0167387 A1 | 7/2007 | Imanishi et al. | |
| 2009/0182136 A1* | 7/2009 | Wengel | C12N 15/111 536/24.5 |
| 2010/0227909 A1* | 9/2010 | Cleary | C12N 15/111 514/44 A |
| 2011/0054011 A1 | 3/2011 | McCullagh et al. | |
| 2012/0263738 A1* | 10/2012 | Brown | A61K 31/713 424/178.1 |

FOREIGN PATENT DOCUMENTS

| | | |
|---|---|---|
| JP | 10-195098 A | 7/1998 |
| JP | 10-304889 A | 11/1998 |
| JP | 2002-521310 A | 7/2002 |
| JP | 2006-522586 A | 10/2006 |
| JP | 2010-537958 A | 12/2010 |
| WO | WO 2004/044181 A2 | 5/2004 |

(Continued)

OTHER PUBLICATIONS

Khoo et al (BMC Molecular Biology 2007, 8:3).*

(Continued)

*Primary Examiner* — Richard A Schnizer
(74) *Attorney, Agent, or Firm* — Foley & Lardner LLP

(57) ABSTRACT

Disclosed are double-stranded antisense nucleic acid complexes that can efficiently alter the processing of RNA in a cell via an antisense effect, and methods for using the same. One method comprises contacting with the cell a double-stranded nucleic acid complex comprising: a first nucleic acid strand annealed to a second nucleic acid strand, wherein: the first nucleic acid strand comprises (i) nucleotides independently selected from natural DNA nucleotides, modified DNA nucleotides, and nucleotide analogs, (ii) no regions that have 4 or more consecutive natural DNA nucleotides, (iii) the total number of natural DNA nucleotides, modified DNA nucleotides, and nucleotide analogs in the first nucleic acid strand is from 8 to 100, and (iv) the first nucleic acid strand is capable of hybridizing to RNA inside of the cell; and the second nucleic acid strand comprises nucleotides independently selected from natural RNA nucleotides, modified RNA nucleotides, and nucleotide analogs.

14 Claims, 11 Drawing Sheets

Specification includes a Sequence Listing.

(56) References Cited

FOREIGN PATENT DOCUMENTS

| WO | WO 2005/021570 A1 | 3/2005 |
|---|---|---|
| WO | WO 2005/113571 A2 | 12/2005 |
| WO | WO 2006/059507 A1 | 6/2006 |
| WO | WO 2007/143315 A2 | 12/2007 |
| WO | WO 2008/029619 A1 | 3/2008 |
| WO | WO 2008/043753 A2 | 4/2008 |
| WO | WO 2008/113830 A1 | 9/2008 |
| WO | WO 2011/139710 A1 | 11/2011 |
| WO | WO 2008/138487 A2 | 10/2012 |
| WO | WO 2012/144906 A1 | 10/2012 |

OTHER PUBLICATIONS

Wang et al (Nature Structural & Molecular Biology 19(10): 1044-1051, 2012).*

Wang et al (Nucleic Acids Research, 2005, 33(16) 5053-5062).*

Hua et al (In Exon Skipping, Human Press, Aartsma-Rus ed. Chapter 20, pp. 307-323, 2012).*

GenBank Accession XM_017012838.1, 2016.*

Baumann et al (Oligonucleotides 19(1), 1-14, 2009) (Year: 2009).*

International Search Report dated Sep. 22, 2014, in PCT/JP2014/003208.

Cirak et al., "Exon skipping and dystrophin restoration in patients with Duchenne muscular dystrophy after systemic phosphorodiamidate morpholino oligomer treatment: an open-label, phase 2, dose-escalation study," The Lancet, 2011, 378:595-605.

Fairclough et al., "Therapy for Duchenne muscular dystrophy: renewed optimism from genetic approaches," Nature Reviews Genetics, Apr. 23, 2013, 373-378.

Goemans et al., "Systemic Administration of PRO051 in Duchenne's Muscular Dystrophy," N. Engl. J. Med., Apr. 21, 2011, 364(16):1513-1522.

Kole et al., "RNA therapeutics: beyond RNA interference and antisense oligonucleotides," Nature Reviews Drug Discovery, Feb. 2012, 11:125-140.

Moreno et al., "A synthetic snRNA $m_3$G-CAP enhances nuclear delivery of exogenous proteins and nucleic acids," Nucleic Acids Research, 2009, 37(6):1925-1935.

Nishina et al. "Efficient In Vivo Delivery of siRNA to the Liver by Conjugation of αTocopherol," Molecular Therapy, Apr. 2008, 16(4):734-740.

Peer et al., "Systemic Leukocyte-Directed siRNA Delivery Revealing Cyclin D1 as an Anti-Inflammatory Target," Science, Feb. 1, 2008, 319:627-630.

Soutschek et al., "Therapeutic silencing of an endogenous gene by systemic administration of modified siRNAs," Nature, Nov. 11, 2004, 432: 173-178.

Yin et al,. "Cell-penetrating peptide-conjugated anitsense oligonucleotides restore systemic muscle and cardiac dystrophin expression and function," Human Molecular Genetics, 2008, 17(24):3909-3918.

Supplementary European Search Report dated Mar. 15, 2017, in EP 14814254.0.

Jekerle et al., "Functional comparison of single- and double-stranded mdr1 antisense oligodeoxynucleotides in human ovarian cancer cell lines," Journal of Pharmacy and Pharmaceutical Sciences, 2005, 8(3):516-527.

* cited by examiner

[Fig. 1]
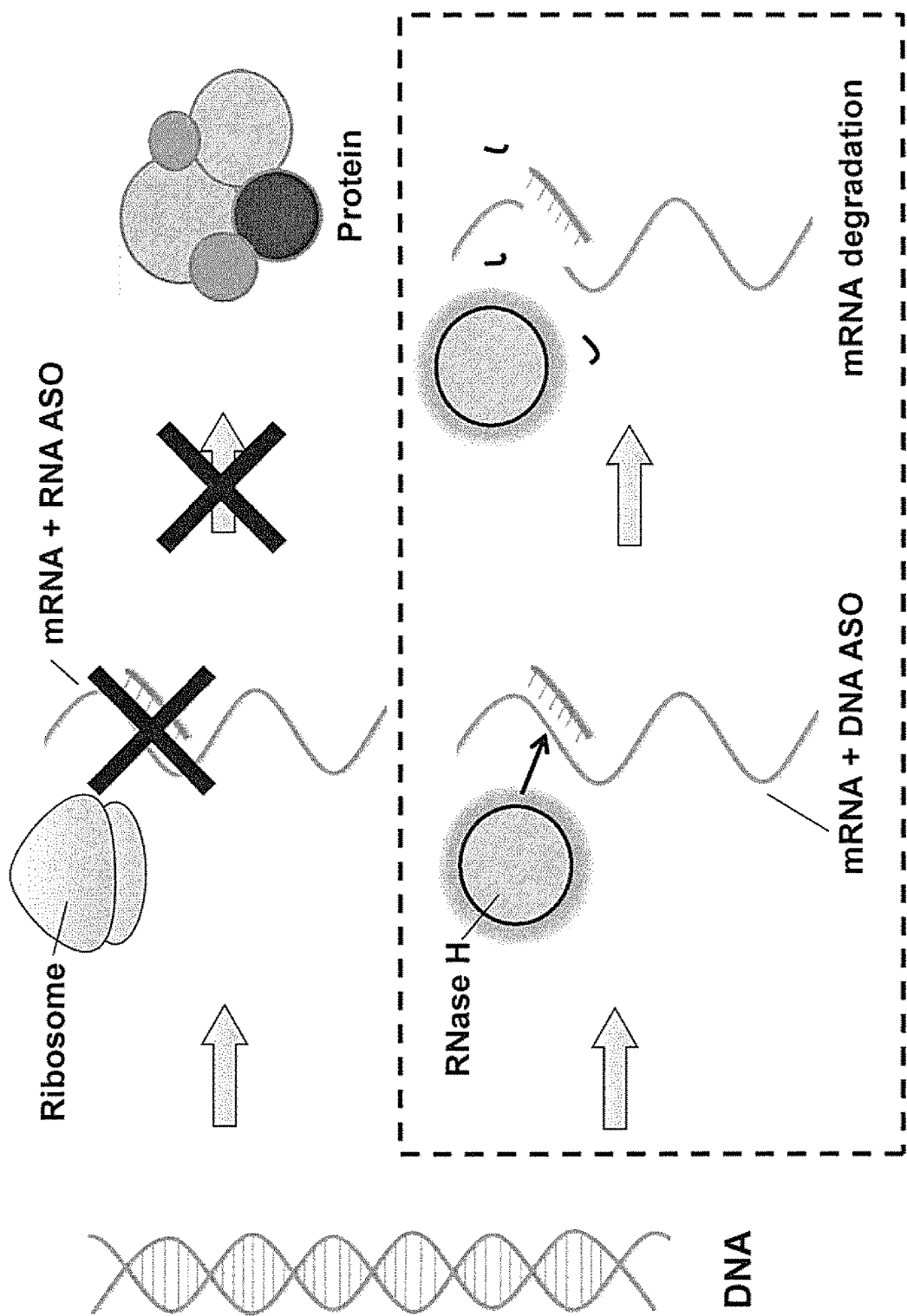

[Fig. 2]
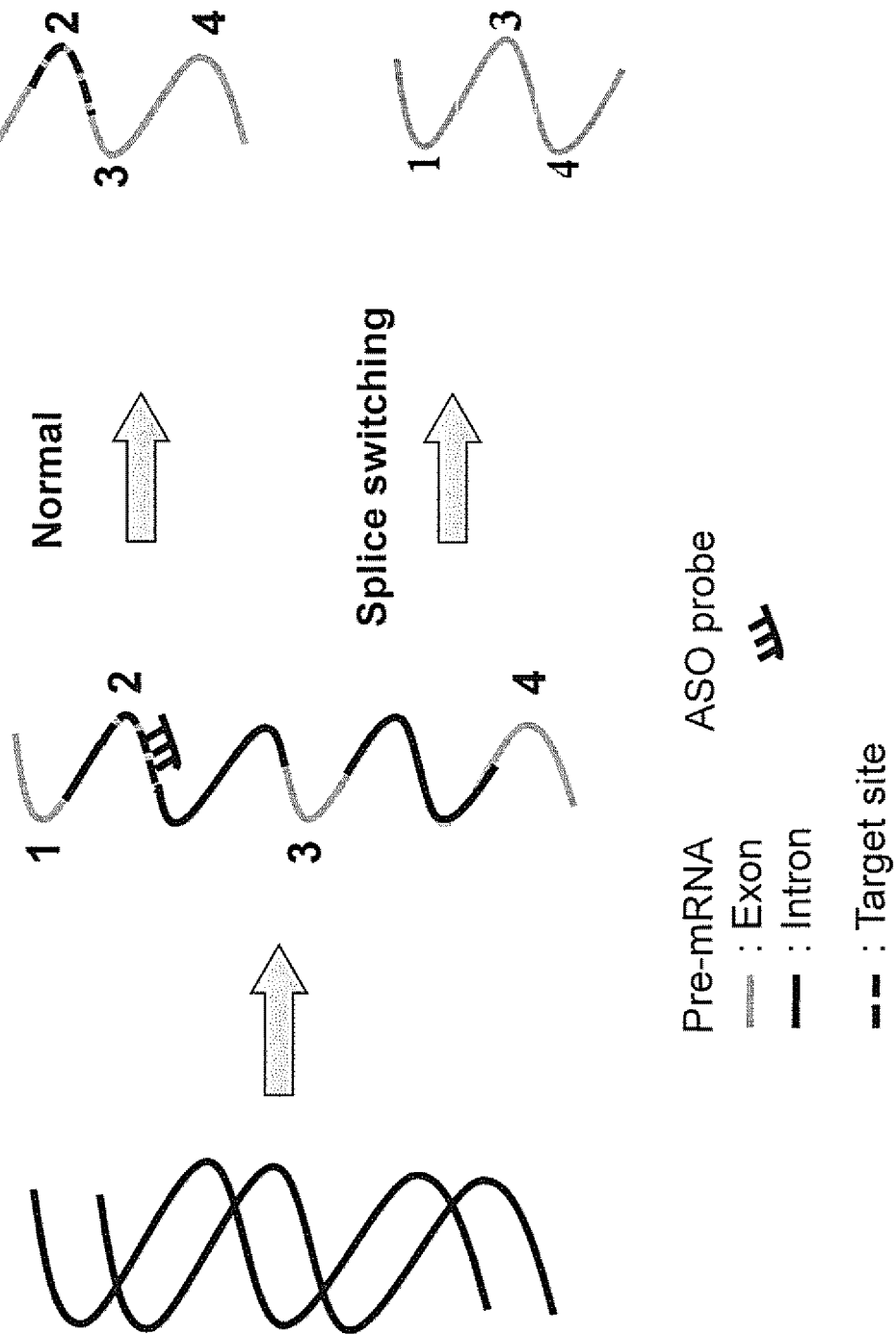

[Fig. 3]
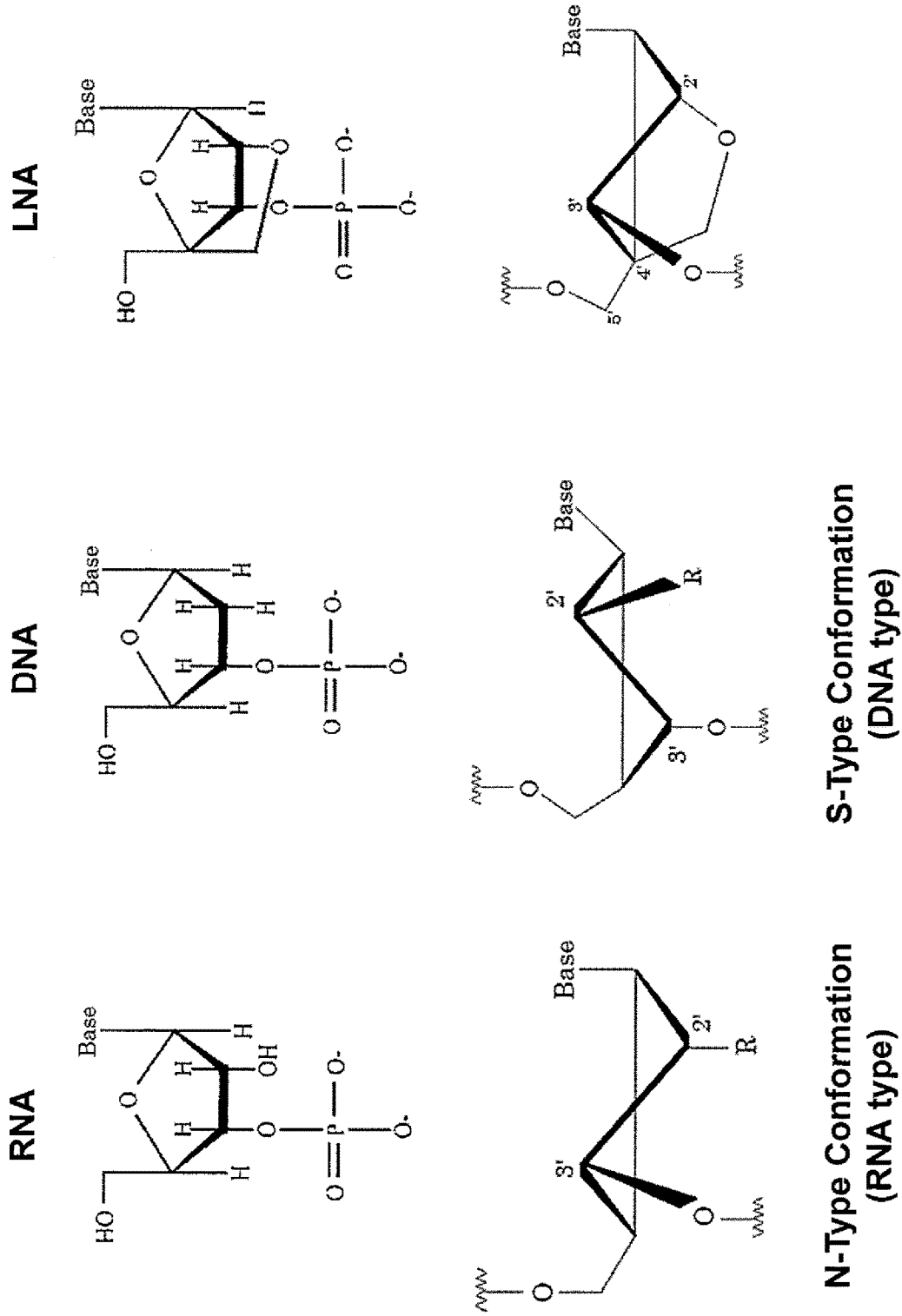

[Fig. 4]
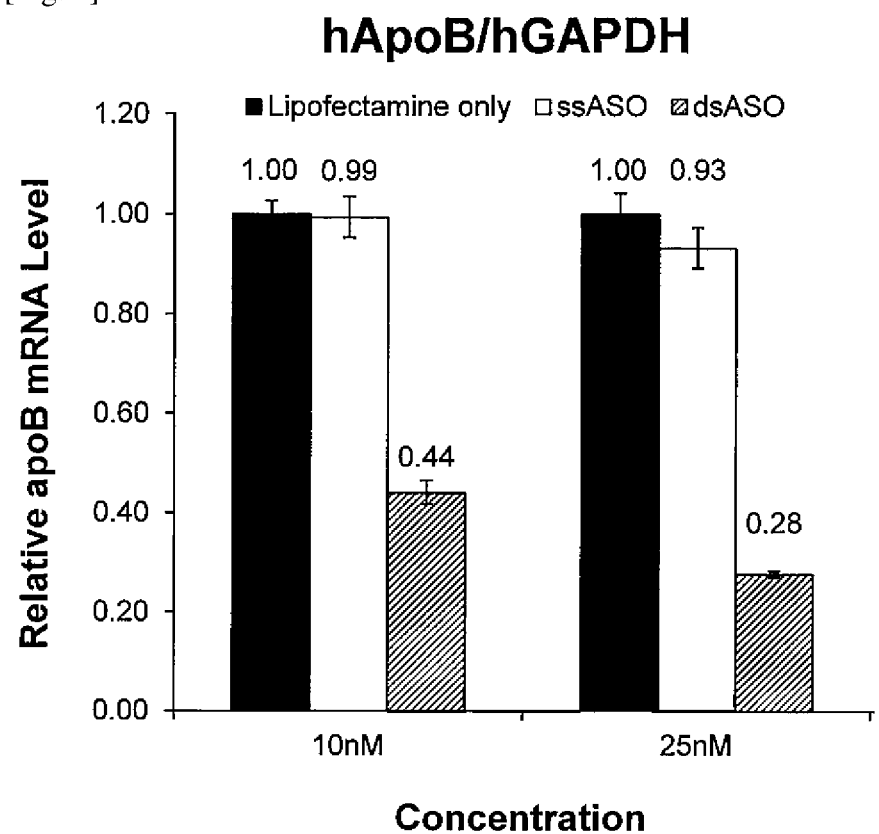

[Fig. 5]
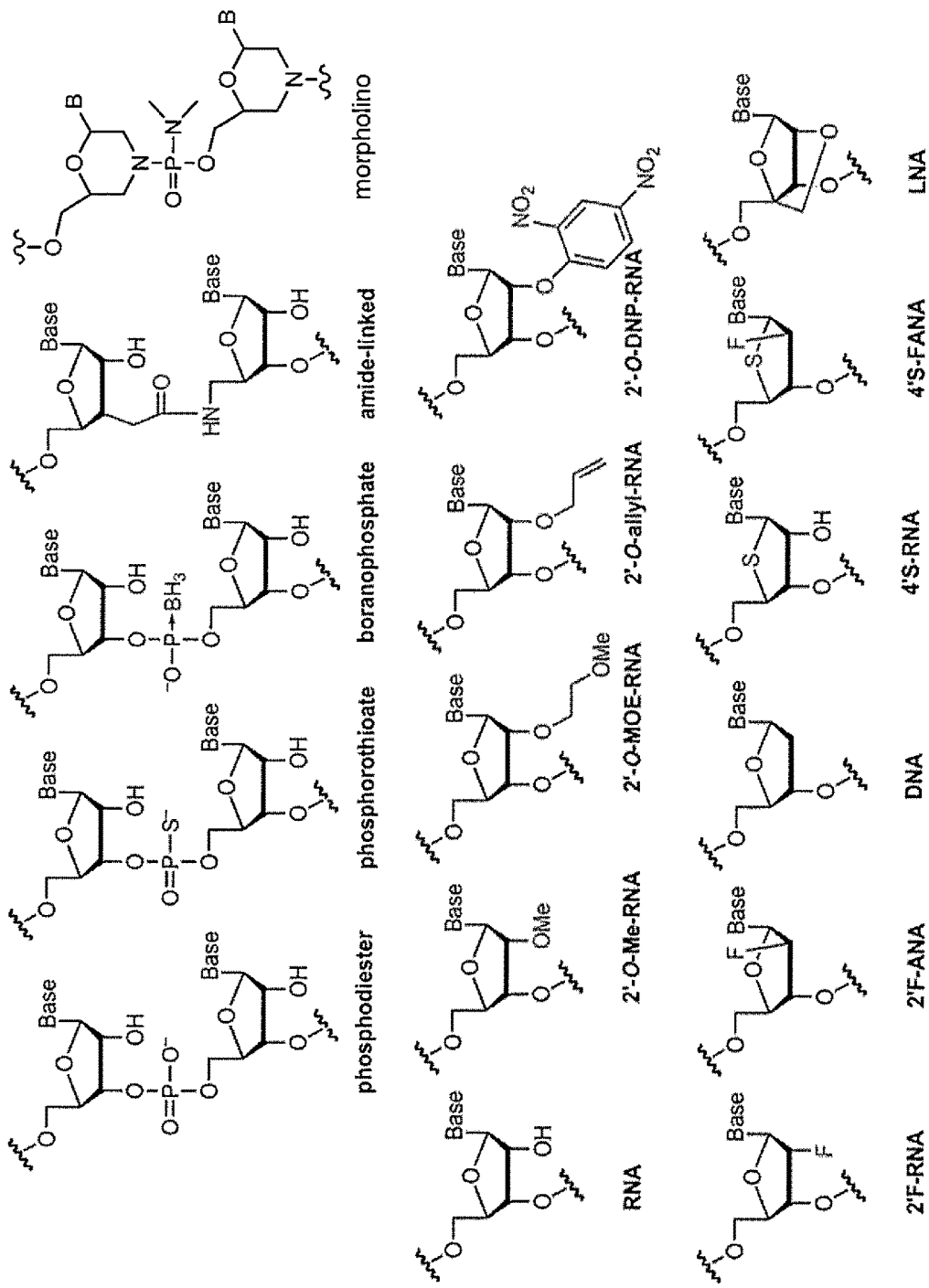

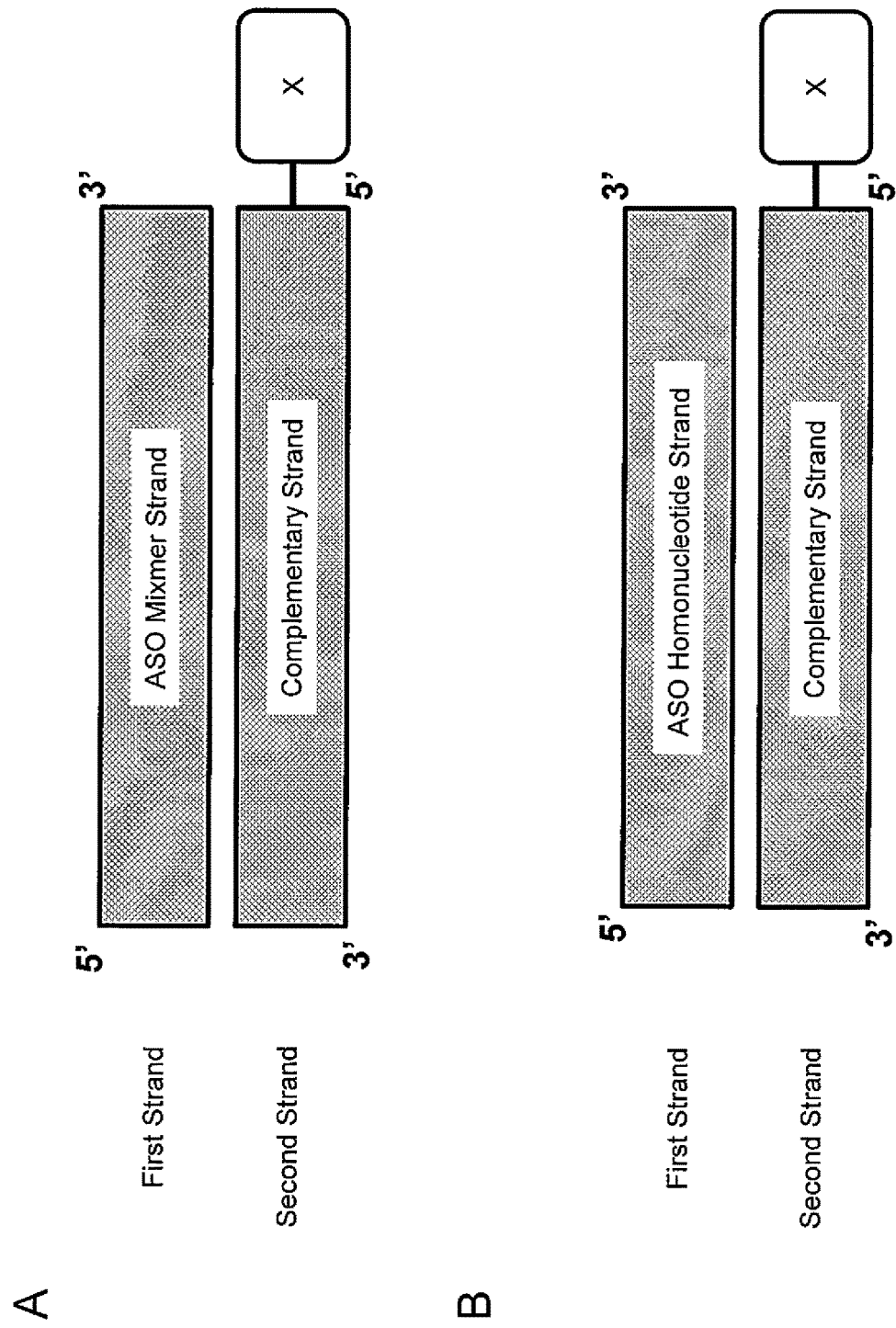
[Fig. 6]

[Fig. 7]
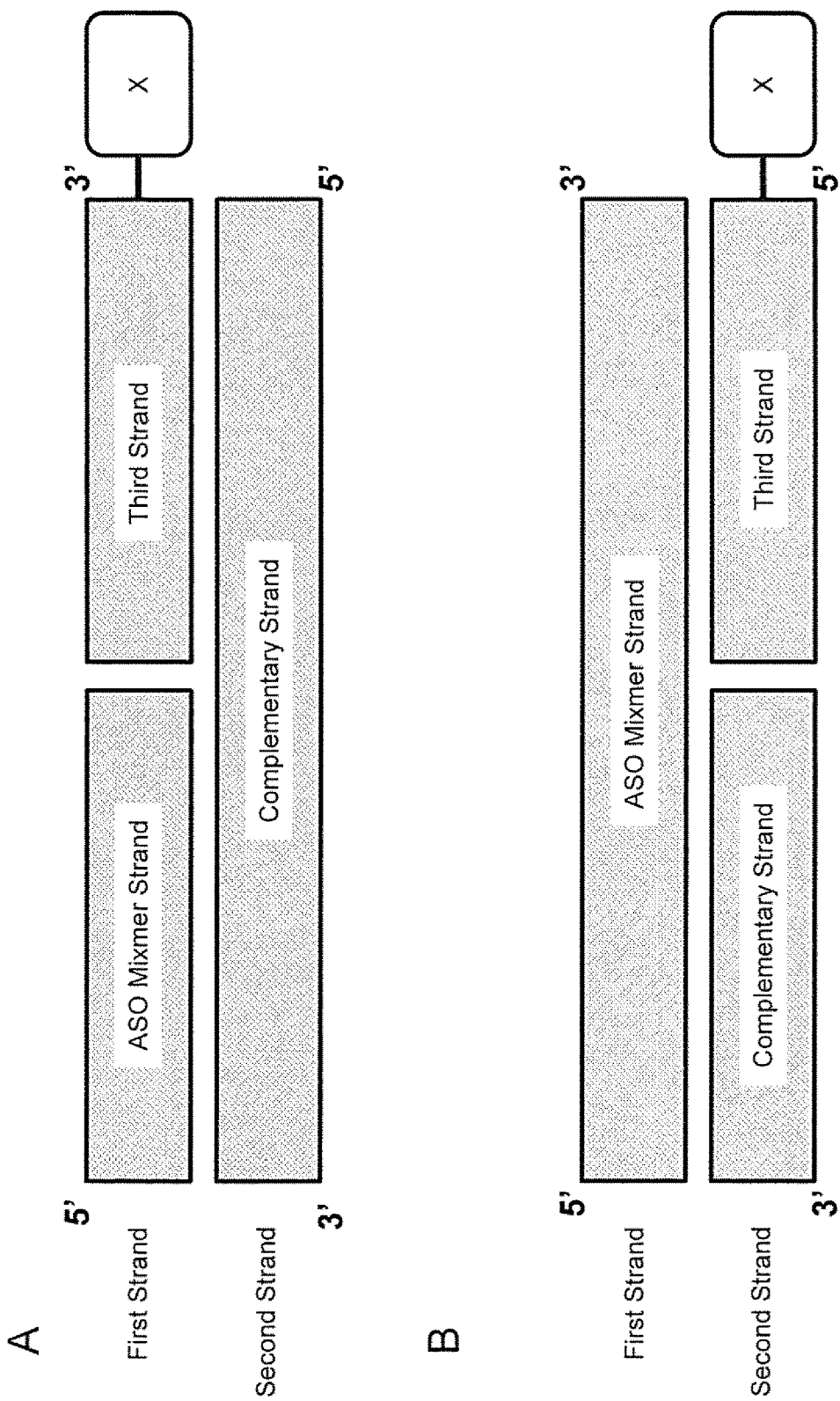

[Fig. 8]
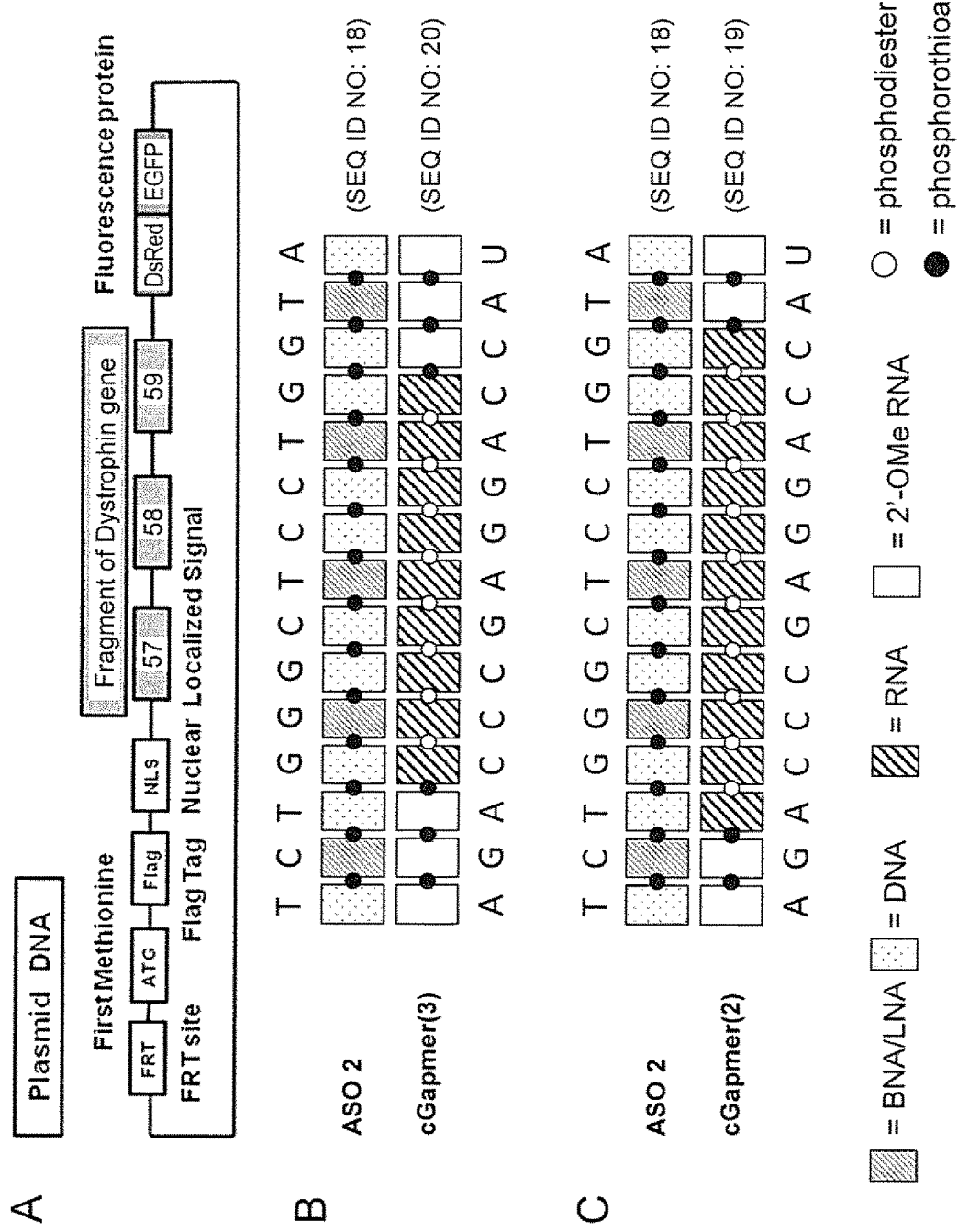

[Fig. 9]
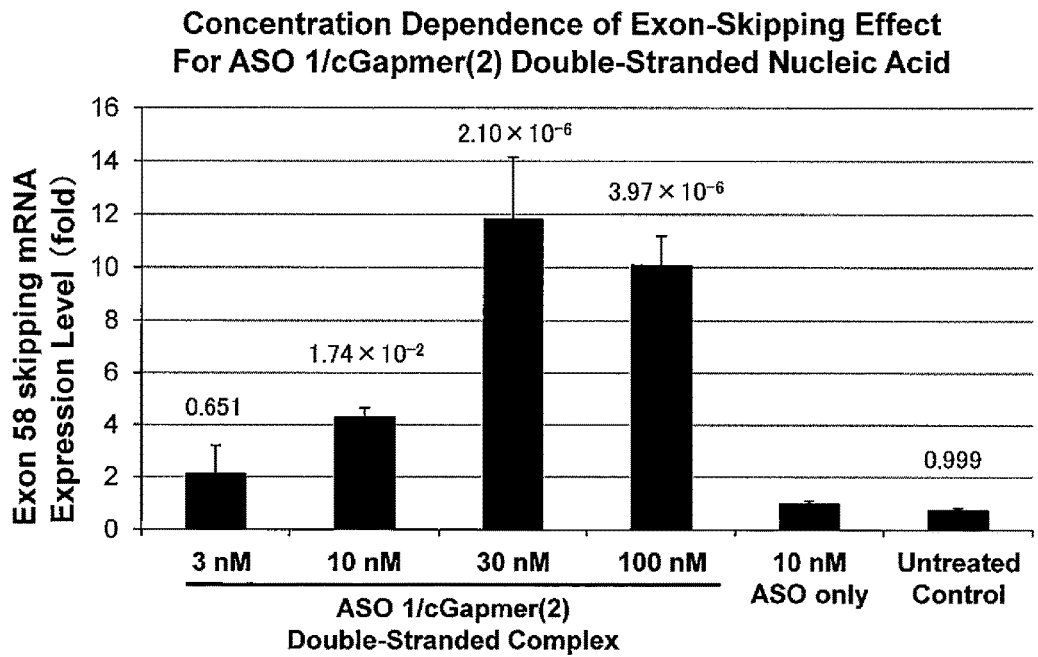
[Fig. 10]
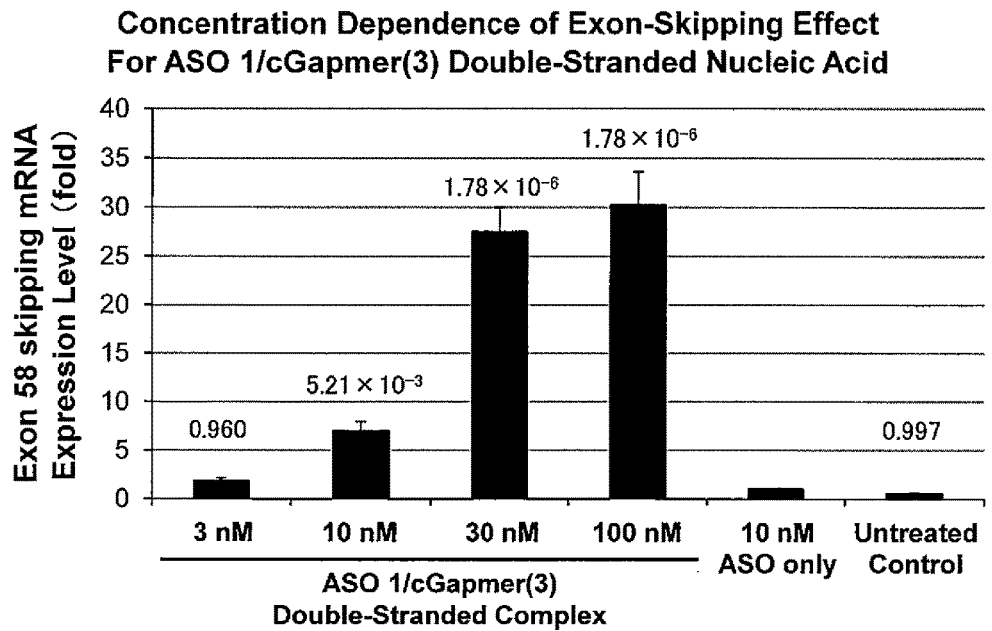

[Fig. 11]
Concentration Dependence of Exon-Skipping Effect For ASO 2/cGapmer(2) Double-Stranded Nucleic Acid
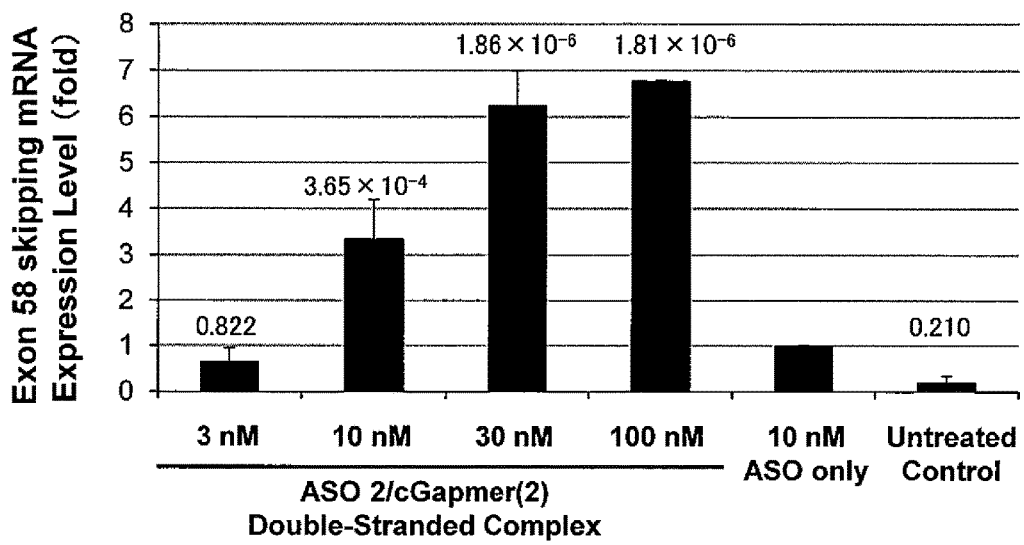
[Fig. 12]
Concentration Dependence of Exon-Skipping Effect For ASO 2/cGapmer(3) Double-Stranded Nucleic Acid
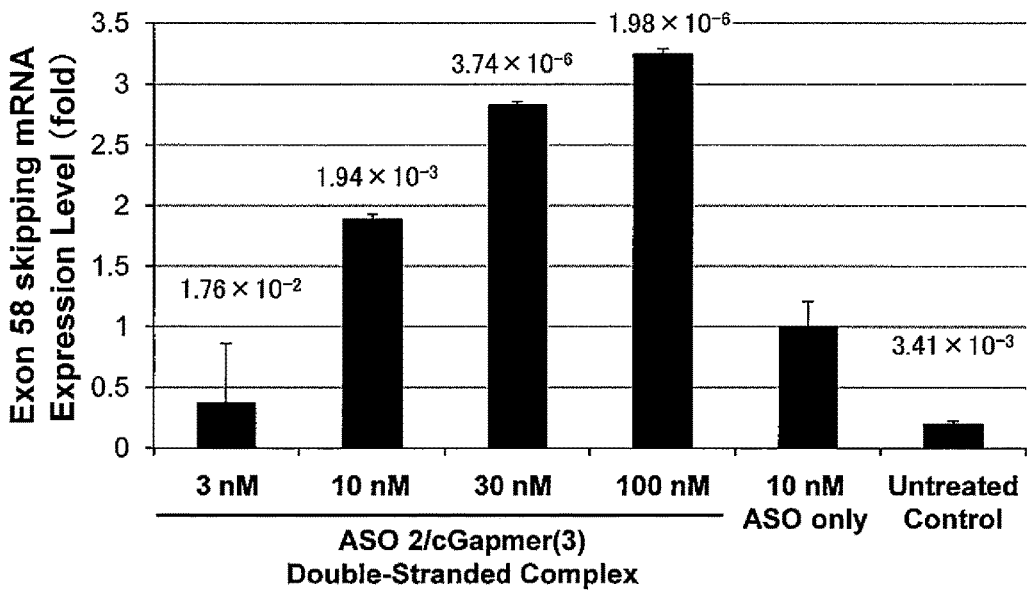

[Fig. 13]
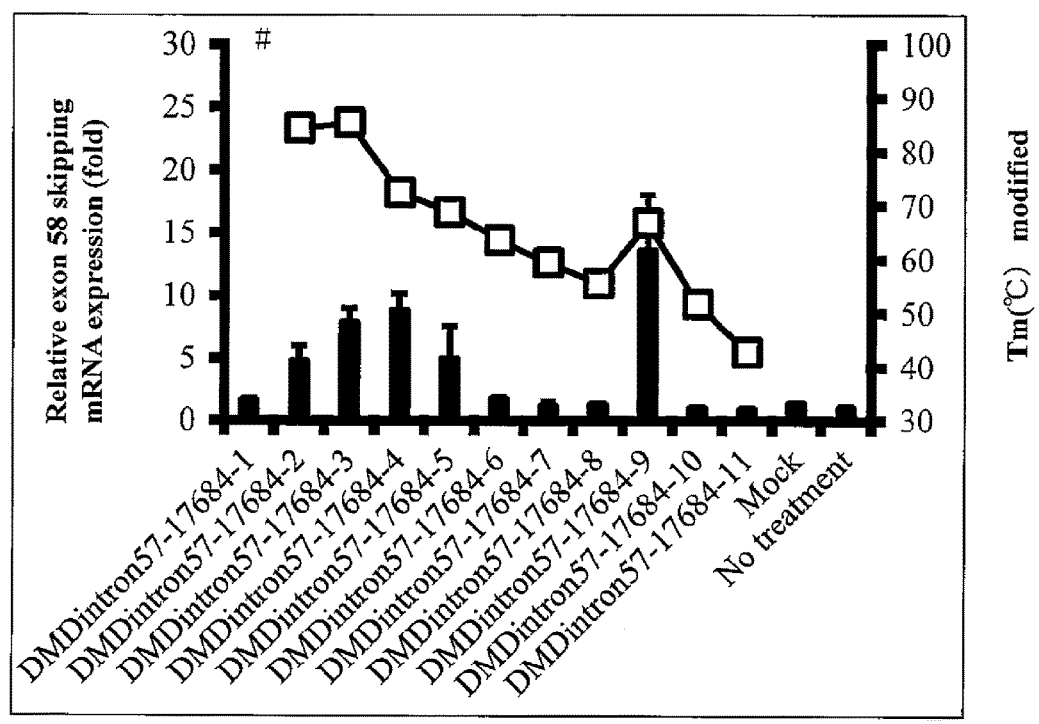

SEQUENCE LISTING

<160> NUMBER OF SEQ ID NOS: 45

<210> SEQ ID NO 1
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12), (12)..(13)
<223> OTHER INFORMATION: Phosphorothioate linkage
<220> FEATURE:
<221> NAME/KEY: misc_feature
<222> LOCATION: (13)..(14), (14)..(15), (15)..(16)
<223> OTHER INFORMATION: Phosphorothioate linkage
<220> FEATURE:
<221> NAME/KEY: misc_feature
<222> LOCATION: (1)..(1), (2)..(2), (3)..(3), (14)..(14), (15)..(15), (16)..(16)
<223> OTHER INFORMATION: LNA
<220> FEATURE:
<221> NAME/KEY: misc_feature
<222> LOCATION: (4)..(4), (5)..(5), (6)..(6), (7)..(7), (8)..(8), (9)..(9)
<223> OTHER INFORMATION: 2-o-Me
<220> FEATURE:
<221> NAME/KEY: misc_feature

```
<222> LOCATION: (10)..(10), (11)..(11), (12)..(12), (13)..(13)
<223> OTHER INFORMATION: 2-o-Me

<400> SEQUENCE: 1
ctcccaccac atagca                                                    16

<210> SEQ ID NO 2
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (13)..(14), (14)..(15),
      (15)..(16)
<223> OTHER INFORMATION: Phosphorothioate linkage
<220> FEATURE:
<221> NAME/KEY: misc_feature
<222> LOCATION: (1)..(1), (2)..(2), (3)..(3), (14)..(14), (15)..(15),
      (16)..(16)
<223> OTHER INFORMATION: 2-o-Me

<400> SEQUENCE: 2
gcuauguggu gggaug                                                    16

<210> SEQ ID NO 3
<211> LENGTH: 42
<212> TYPE: DNA
<213> ORGANISM: Artificial
<220> FEATURE:
<223> OTHER INFORMATION: Synthetic

<400> SEQUENCE: 3
agcttaccat ggattacaag gacgacgacg acaaggggt ac                        42

<210> SEQ ID NO 4
<211> LENGTH: 34
<212> TYPE: DNA
<213> ORGANISM: Artificial
<220> FEATURE:
<223> OTHER INFORMATION: Synthetic

<400> SEQUENCE: 4
ccccttgtcg tcgtcgtcct tgtaatccat ggta                                34

<210> SEQ ID NO 5
<211> LENGTH: 29
<212> TYPE: DNA
<213> ORGANISM: Artificial
<220> FEATURE:
<223> OTHER INFORMATION: Primer

<400> SEQUENCE: 5
cccgggtgtg agcaagggcg aggagctgt                                      29

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
atagggccct tacttgtaca gctcgtccat                                     30

<210> SEQ ID NO 7
```

```
<211> LENGTH: 39
<212> TYPE: DNA
<213> ORGANISM: Artificial
<220> FEATURE:
<223> OTHER INFORMATION: Primer

<400> SEQUENCE: 7
atatggatcc aaccggtgtg gcctcctccg aggacgtca                    39

<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8
cggtctacag gaacaggtgg tggc                                   24

<210> SEQ ID NO 9
<211> LENGTH: 47
<212> TYPE: DNA
<213> ORGANISM: Artificial
<220> FEATURE:
<223> OTHER INFORMATION: Synthetic

<400> SEQUENCE: 9
atgccccaaa aaaaaaacgc aaagtggagg acccaaaggt accaaag           47

<210> SEQ ID NO 10
<211> LENGTH: 55
<212> TYPE: DNA
<213> ORGANISM: Artificial
<220> FEATURE:
<223> OTHER INFORMATION: Synthetic

<400> SEQUENCE: 10
gatcctttgg tacctttggg tcctccactt tgcgtttttt ttttggggca tgtac  55

<210> SEQ ID NO 11
<211> LENGTH: 29
<212> TYPE: DNA
<213> ORGANISM: Artificial
<220> FEATURE:
<223> OTHER INFORMATION: Primer

<400> SEQUENCE: 11
aacggtacca acgctgctgt tcttttttca                             29

<210> SEQ ID NO 12
<211> LENGTH: 33
<212> TYPE: DNA
<213> ORGANISM: Artificial
<220> FEATURE:
<223> OTHER INFORMATION: Primer

<400> SEQUENCE: 12
gtgtttgtaa tggacgattt cttaaagggt att                         33

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
```
aaatcgtcca ttacaaacac agcgctttcc                                              30

<210> SEQ ID NO 14
<211> LENGTH: 29
<212> TYPE: DNA
<213> ORGANISM: Artificial
<220> FEATURE:
<223> OTHER INFORMATION: Primer

<400> SEQUENCE: 14
agaccggtac tcctcagcct gctttcgta                                               29

<210> SEQ ID NO 15
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (2)..(2), (5)..(5), (8)..(8), (11)..(11), (14)..(14)
<223> OTHER INFORMATION: LNA

<400> SEQUENCE: 15
ccctcttgaa ggcct                                                              15

<210> SEQ ID NO 16
<211> LENGTH: 15
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (14)..(15)
<223> OTHER INFORMATION: Phosphorothioate linkage
<220> FEATURE:
<221> NAME/KEY: misc_feature
<222> LOCATION: (1)..(1), (2)..(2), (14)..(14), (15)..(15)
<223> OTHER INFORMATION: 2-o-Me

<400> SEQUENCE: 16
aggccuucaa gaggg                                                              15

<210> SEQ ID NO 17
<211> LENGTH: 15
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (13)..(14), (14)..(15)
<223> OTHER INFORMATION: Phosphorothioate linkage
<220> FEATURE:
<221> NAME/KEY: misc_feature
<222> LOCATION: (1)..(1), (2)..(2), (3)..(3), (13)..(13), (14)..(14),

```
      (15)..(15)
<223> OTHER INFORMATION: 2-o-Me

<400> SEQUENCE: 17
aggccuucaa gaggg                                                     15

<210> SEQ ID NO 18
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (2)..(2), (5)..(5), (8)..(8), (11)..(11), (14)..(14)
<223> OTHER INFORMATION: LNA

<400> SEQUENCE: 18
tctgggctcc tggta                                                     15

<210> SEQ ID NO 19
<211> LENGTH: 15
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (14)..(15)
<223> OTHER INFORMATION: Phosphorothioate linkage
<220> FEATURE:
<221> NAME/KEY: misc_feature
<222> LOCATION: (1)..(1), (2)..(2), (14)..(14), (15)..(15)
<223> OTHER INFORMATION: 2-o-Me

<400> SEQUENCE: 19
uaccaggagc ccaga                                                     15

<210> SEQ ID NO 20
<211> LENGTH: 15
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (13)..(14), (14)..(15)
<223> OTHER INFORMATION: Phosphorothioate linkage
<220> FEATURE:
<221> NAME/KEY: misc_feature
<222> LOCATION: (1)..(1), (2)..(2), (3)..(3), (13)..(13), (14)..(14),
      (15)..(15)
<223> OTHER INFORMATION: 2-o-Me

<400> SEQUENCE: 20
uaccaggagc ccaga                                                     15
```

```
<210> SEQ ID NO 21
<211> LENGTH: 18
<212> TYPE: DNA
<213> ORGANISM: Artificial
<220> FEATURE:
<223> OTHER INFORMATION: Primer

<400> SEQUENCE: 21
tcagcctgct ttcgtaga                                                 18

<210> SEQ ID NO 22
<211> LENGTH: 21
<212> TYPE: DNA
<213> ORGANISM: Artificial
<220> FEATURE:
<223> OTHER INFORMATION: Primer

<400> SEQUENCE: 22
gatgtacata ggagctgcct c                                             21

<210> SEQ ID NO 23
<211> LENGTH: 19
<212> TYPE: DNA
<213> ORGANISM: Artificial
<220> FEATURE:
<223> OTHER INFORMATION: Primer

<400> SEQUENCE: 23
ggtcaccagg gctgctttt                                                19

<210> SEQ ID NO 24
<211> LENGTH: 28
<212> TYPE: DNA
<213> ORGANISM: Artificial
<220> FEATURE:
<223> OTHER INFORMATION: Primer

<400> SEQUENCE: 24
gtaaaccatg tagttgaggt caatgaag                                      28

<210> SEQ ID NO 25
<211> LENGTH: 29
<212> TYPE: DNA
<213> ORGANISM: Artificial
<220> FEATURE:
<223> OTHER INFORMATION: Primer

<400> SEQUENCE: 25
aacggtacca acgctgctgt tcttttttca                                    29

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
cttggagccg tactggaact                                               20

<210> SEQ ID NO 27
<211> LENGTH: 20
<212> TYPE: DNA
<213> ORGANISM: Artificial
<220> FEATURE:
<223> OTHER INFORMATION: Primer
```

```
<400> SEQUENCE: 27
accacagtcc atgccatcac                                              20

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
tccaccaccc tgttgctgta                                              20

<210> SEQ ID NO 29
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5), (6)..
      (6)
<223> OTHER INFORMATION: LNA
<220> FEATURE:
<221> NAME/KEY: misc_feature
<222> LOCATION: (7)..(7), (8)..(8), (9)..(9), (10)..(10), (11)..(11),
      (12)..(12)
<223> OTHER INFORMATION: LNA
<220> FEATURE:
<221> NAME/KEY: misc_feature
<222> LOCATION: (13)..(13), (14)..(14), (15)..(15)
<223> OTHER INFORMATION: LNA

<400> SEQUENCE: 29
tccctcttga aggcc                                                   15

<210> SEQ ID NO 30
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
```

```
<222> LOCATION: (1)..(1), (3)..(3), (5)..(5), (7)..(7), (9)..(9), (11)..
      (11)
<223> OTHER INFORMATION: LNA
<220> FEATURE:
<221> NAME/KEY: misc_feature
<222> LOCATION: (13)..(13), (15)..(15)
<223> OTHER INFORMATION: LNA

<400> SEQUENCE: 30
tccctcttga aggcc                                                      15

<210> SEQ ID NO 31
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (2)..(2), (4)..(4), (6)..(6), (8)..(8), (10)..(10),
      (12)..(12)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 31
tccctcttga aggcc                                                      15

<210> SEQ ID NO 32
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (3)..(3), (6)..(6), (9)..(9), (12)..(12), (15)..(15)
<223> OTHER INFORMATION: LNA

<400> SEQUENCE: 32
tccctcttga aggcc                                                      15

<210> SEQ ID NO 33
```

```
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (3)..(3), (6)..(6), (12)..(12), (15)..(15)
<223> OTHER INFORMATION: LNA
<220> FEATURE:
<221> NAME/KEY: misc_feature
<222> LOCATION: (9)..(9)
<223> OTHER INFORMATION: 2-o-Me

<400> SEQUENCE: 33
tccctcttga aggcc                                                    15

<210> SEQ ID NO 34
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (3)..(3), (9)..(9), (15)..(15)
<223> OTHER INFORMATION: LNA
<220> FEATURE:
<221> NAME/KEY: misc_feature
<222> LOCATION: (6)..(6), (12)..(12)
<223> OTHER INFORMATION: 2-o-Me

<400> SEQUENCE: 34
tccctcttga aggcc                                                    15

<210> SEQ ID NO 35
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
```

<221> NAME/KEY: misc_feature
<222> LOCATION: (7)..(8), (8)..(9), (9)..(10), (10)..(11), (11)..(12), (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (3)..(3), (15)..(15)
<223> OTHER INFORMATION: LNA
<220> FEATURE:
<221> NAME/KEY: misc_feature
<222> LOCATION: (6)..(6), (9)..(9), (12)..(12)
<223> OTHER INFORMATION: 2-o-Me

<400> SEQUENCE: 35
tccctcttga aggcc                                                    15

<210> SEQ ID NO 36
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12), (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (3)..(3), (6)..(6), (12)..(12), (15)..(15)
<223> OTHER INFORMATION: 2-o-Me

<400> SEQUENCE: 36
tccctcttga aggcc                                                    15

<210> SEQ ID NO 37
<211> LENGTH: 15
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..(7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12), (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5), (6)..

```
        (6)
<223> OTHER INFORMATION: 2-o-Me
<220> FEATURE:
<221> NAME/KEY: misc_feature
<222> LOCATION: (7)..(7), (8)..(8), (9)..(9), (10)..(10), (11)..(11),
      (12)..(12)
<223> OTHER INFORMATION: 2-o-Me
<220> FEATURE:
<221> NAME/KEY: misc_feature
<222> LOCATION: (13)..(13), (14)..(14), (15)..(15)
<223> OTHER INFORMATION: 2-o-Me

<400> SEQUENCE: 37
ucccucuuga aggcc                                                    15

<210> SEQ ID NO 38
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage
<220> FEATURE:
<221> NAME/KEY: misc_feature
<222> LOCATION: (3)..(3), (6)..(6), (9)..(9), (12)..(12), (15)..(15)
<223> OTHER INFORMATION: 2-o-Me

<400> SEQUENCE: 38
tccctcttga aggcc                                                    15

<210> SEQ ID NO 39
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6), (6)..
      (7)
<223> OTHER INFORMATION: Phosphorothioate linkage
<220> FEATURE:
<221> NAME/KEY: misc_feature
<222> LOCATION: (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (13)..(14), (14)..(15)
<223> OTHER INFORMATION: Phosphorothioate linkage

<400> SEQUENCE: 39
tccctcttga aggcc                                                    15

<210> SEQ ID NO 40
<211> LENGTH: 15
<212> TYPE: RNA
<213> ORGANISM: Artificial
<220> FEATURE:
<223> OTHER INFORMATION: Synthetic
```

<400> SEQUENCE: 40
ggccuucaag aggga 15

<210> SEQ ID NO 41
<211> LENGTH: 15
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (14)..(15)
<223> OTHER INFORMATION: Phosphorothioate linkage
<220> FEATURE:
<221> NAME/KEY: misc_feature
<222> LOCATION: (1)..(1), (2)..(2), (14)..(14), (15)..(15)
<223> OTHER INFORMATION: 2-o-Me

<400> SEQUENCE: 41
ggccuucaag aggga 15

<210> SEQ ID NO 42
<211> LENGTH: 21
<212> TYPE: DNA
<213> ORGANISM: Artificial
<220> FEATURE:
<223> OTHER INFORMATION: Primer

<400> SEQUENCE: 42
gatgtacata ggagctgcct c 21

<210> SEQ ID NO 43
<211> LENGTH: 18
<212> TYPE: DNA
<213> ORGANISM: Artificial
<220> FEATURE:
<223> OTHER INFORMATION: Primer

<400> SEQUENCE: 43
tcagcctgct ttcgtaga 18

<210> SEQ ID NO 44
<211> LENGTH: 19
<212> TYPE: DNA
<213> ORGANISM: Artificial
<220> FEATURE:
<223> OTHER INFORMATION: Primer

<400> SEQUENCE: 44
ggtcaccagg gctgctttt 19

<210> SEQ ID NO 45
<211> LENGTH: 28
<212> TYPE: DNA
<213> ORGANISM: Artificial
<220> FEATURE:
<223> OTHER INFORMATION: Primer

<400> SEQUENCE: 45
gtaaaccatg tagttgaggt caatgaag 28

DOUBLE-STRANDED ANTISENSE NUCLEIC ACID WITH EXON-SKIPPING EFFECT

CROSS-REFERENCE TO RELATED APPLICATIONS

This application is a National Stage application of PCT/JP2014/003208, filed Jun. 16, 2014, which claims priority from U.S. Provisional Application Nos. 61/835,634, filed Jun. 16, 2013, and 61/836,672, filed Jun. 19, 2013.

TECHNICAL FIELD

This application relates to a double-stranded nucleic acid having an activity of changing the function of coding or non-coding RNA, and more particularly, an effect of suppressing the expression of a target gene by means of an antisense effect and an effect brought about by exon-skipping and so on. The double-stranded nucleic acid includes one strand that acts as an antisense oligonucleotide that is complementary to RNA in a cell. Such RNA may be part of a coding or a non-coding region, or a part of an exon or an intron.

BACKGROUND ART

In recent years, oligonucleotides have been a subject of interest in the on-going development of pharmaceutical products called nucleic acid drugs, and particularly, from the viewpoints of high selectivity of target gene and low toxicity, the development of nucleic acid drugs utilizing an antisense method is actively underway. The antisense method is a method of selectively altering the expression of a protein that is encoded by a target gene, by introducing into a cell an oligonucleotide (antisense oligonucleotide (ASO)) which is complementary to a partial sequence of the mRNA (sense strand) of a target gene.

As illustrated in FIG. 1 (upper portion), when an oligonucleotide comprising an RNA is introduced into a cell as an ASO, the ASO binds to a transcription product (mRNA) of the target gene, and a partial double strand is formed. It is known that this double strand plays a role as a cover to prevent translation by a ribosome, and thus the expression of the protein encoded by the target gene is inhibited.

On the other hand, when an oligonucleotide comprising a DNA is introduced into a cell as an ASO, a partial DNA-RNA hetero-duplex is formed. Since this structure is recognized by RNase H, and the mRNA of the target gene is thereby decomposed, the expression of the protein encoded by the target gene is inhibited. (FIG. 1, lower portion). Furthermore, it has been also found that in many cases, the gene expression suppressing effect is higher in the case of using a DNA as an ASO (RNase H-dependent route), as compared with the case of using an RNA.

On the occasion of utilizing an oligonucleotide as a nucleic acid drug, various nucleic acid analogs such as Locked Nucleic Acid (LNA) (registered trademark), other bridged nucleic acids, and the like have been developed in consideration of an enhancement of the binding affinity to a target RNA, stability in vivo, and the like.

Antisense oligonucleotides can be applied to induce exon skipping during the processing of pre-mRNA. The concept is illustrated in FIG. 2. The figure shows a double-stranded DNA segment, and transcription of the DNA yields a pre-mRNA consisting of exons (coding regions) and introns (non-coding regions). Generally, before the mRNA is translated into a peptide (protein) sequence, the cell processes the pre-mRNA to remove the intron regions. It is known that antisense oligonucleotides that target and bind to the pre-mRNA can induce the cell to not include (skip over) an exon. As shown in FIG. 2, the pre-mRNA includes exons 1, 2, 3, and 4. Under normal operation, without an ASO present, the introns would be removed and exons 1, 2, 3, and 4 would be spliced together to yield a full length mRNA.

However, in the presence of an ASO that binds to a target site, illustrated here as being in exon 2, the cell will, in addition to removing the introns, exclude exon 2 to yield a truncated splice-switched mRNA of exons 1, 3, and 4.

As is well-known in the art, exon skipping and splice switching is of interest for treating or ameliorating the effects of genetic mutations. Certain genetic diseases are thought to be treatable at the genetic level by such a mechanism, rather than at the protein level. Two examples are Duchenne muscular dystrophy and spinal muscular dystrophy (Non-Patent Documents 1-4).

Whereas siRNA and gapmer antisense oligonucleotides act to suppress gene expression, splice-switching oligonucleotides (SSOs) act to modify pre-mRNA splicing. Such oligonucleotides can "repair" RNA that would otherwise not be processed correctly, or, they can induce the formation of novel proteins. Because splice variant proteins constitute a large portion of the proteins in humans, the ability to induce and/or modulate splice-switching is the subject of great interest.

Oligonucleotides used as antisense agents usually contain modified nucleotides or nucleotide analogues in order to enhance binding affinity to the targeted sequence. As illustrated in FIG. 3, since the sugar moiety of a natural nucleic acid (RNA or DNA) has a five-membered ring with four carbon atoms and one oxygen atom, the sugar moiety has two kinds of conformations, an N-form and an S-form. It is known that these conformations swing from one to the other, and thereby, the helical structure of the nucleic acid also adopts different forms, an A-form and a B-form. Since the mRNA that serves as the target of the aforementioned ASO adopts a helical structure in the A-form, with the sugar moiety being mainly in the N-form, it is important for the sugar moiety of the ASO to adopt the N-form from the viewpoint of increasing the affinity to RNA. A product that has been developed under this concept is a modified nucleic acid such as a LNA (2'-O,4'-C-methylene-bridged nucleic acid (2',4'-BNA)). For example, in the LNA, as the oxygen at the 2'-position and the carbon at the 4'-position are bridged by a methylene group, the conformation is fixed to the N-form, and there is no more fluctuation between the conformations. Therefore, an oligonucleotide synthesized by incorporating several units of LNA has very high affinity to RNA and very high sequence specificity, and also exhibits excellent heat resistance and nuclease resistance, as compared with oligonucleotides synthesized with conventional natural nucleic acids (see Patent Document 1). Since other artificial nucleic acids also have such characteristics, much attention has been paid to artificial nucleic acids in connection with the utilization of an antisense method and the like (see Patent Documents 1 to 7).

Furthermore, when an oligonucleotide is applied to a drug, it is important that the relevant oligonucleotide can be delivered to the target site with high specificity and high efficiency. Cell-penetrating peptides, such as the short, positively-charged arginine-rich peptides P007 and B peptide, can improve the uptake of oligonucleotides into cells when conjugated to the oligonucleotide (Non-Patent Document 5). Even if an oligonucleotide enters a cell, for it to have a splice-switching effect the oligonucleotide needs to enter the nucleus. Delivery of a splice-switching oligonucleotide across the nuclear membrane remains a challenge (Non-Patent Document 6). It is an object of the invention to provide double-stranded nucleic acid agents that provide enhanced delivery of antisense oligonucleotides into cell nuclei. It is a further object of the invention to provide oligonucleotides that provide enhanced levels of exon skipping and/or alternative spliced processing of pre-mRNA.

In addition, as methods for delivering an oligonucleotide to certain body regions, a method of utilizing lipids such as cholesterol and vitamin E (Non-Patent Documents 7 and 8), a method of utilizing a receptor-specific peptide such as RVG-9R (Non-Patent Document 9), and a method of utilizing an antibody specific to the target site (Non-Patent Document 10) have been developed.

CITATION LIST

Patent Literature

{PTL 1} JP 10-304889 A
{PTL 2} WO 2005/021570
{PTL 3} JP 10-195098 A
{PTL 4} JP 2002-521310 W
{PTL 5} WO 2007/143315
{PTL 6} WO 2008/043753
{PTL 7} WO 2008/029619

Non Patent Literature

{NPL 1} Non-Patent Document 1: Ryszard Kole et al., Nature Reviews, Vol. 11, 125-140 (2012)
{NPL 2} Nathalie M. Goemans et al., New England J. Med., Vol. 364, 1513-1522 (2011)
{NPL 3} Rebecca J. Fairclough et al., Nature Rev. Genetics, doi:10.1038/nrg3460, Apr. 23, 2013, 6 pages.
{NPL 4} Sebahattin Cirak et al., Lancet, Vol. 378, 595-605 (2011)
{NPL 5} HaiFang Yin et al., Human Molecular Genetics, Vol. 17(24), 3909-3918 (2008)
{NPL 6} Pedro M. D. Moreno et al., Nucleic Acids Res., Vol. 37, 1925-1935 (2009)
{NPL 7} Kazutaka Nishina et al., Molecular Therapy, Vol. 16, 734-740 (2008)
{NPL 8} Jurgen Soutscheck et al., Nature, Vol. 432, 173-178 (2004)
{NPL 9} Kazutaka Nishina et al., Molecular Therapy, Vol. 16, 734-740 (2008)
{NPL 10} Dan Peer et al., Science, Vol. 319, 627-630 (2008)

SUMMARY OF INVENTION

Technical Problem

An object of the present invention is to provide a double-stranded nucleic acid agent that can change the function of a coding or non-coding RNA.

Solution to Problem

In certain embodiments, a double-stranded nucleic acid complex comprises an antisense nucleic acid which induces splice-switched variants of RNA. In some embodiments the antisense nucleic acid changing the function of a coding or non-coding RNA. In some embodiments the antisense nucleic acid modulates the processing of RNA. In some embodiments the double-stranded nucleic acid complex delivers the antisense nucleic acid strand to a target region with high specificity and high efficiency. In some embodiments the antisense nucleic acid is delivered inside a cell nucleus with high efficiency.

The inventors investigated the delivery of oligonucleotide agents to a cell nucleus and found that double-stranded antisense oligonucleotides, but not single-stranded oligonucleotides, may have an intracellular transfer mechanism from the cytosol into the nucleus. The results of an experiment comparing the gene silencing effect of a double-stranded agent vs. a single-stranded agent are shown in FIG. 4. The experiment is described in detail below as Example 1. Briefly, an LNA/DNA gapmer antisense oligonucleotide targeting an intron of ApoB pre-mRNA was prepared. A complementary 2'-OMe RNA/RNA gapmer was also prepared, and annealed to the LNA/DNA gapmer to yield a double-stranded nucleic acid agent. Human cells were transfected with either the double-stranded agent (dsASO) or the single-strand LNA/DNA gapmer (ssASO) using Lipofectamine RNAiMAX. The amount of ApoB expressed, normalized to the amount of GAPDH expressed, was measured. Surprisingly, the dsASO agent suppressed the amount of ApoB expressed whereas the single-stranded agent had nearly no effect on the expression level (FIG. 4). Although RNAiMAX can transport the oligonucleotide into a cell, it is not effective for bringing the oligonucleotide into the nucleus. Thus, the difference observed between the double-stranded agent and the single-stranded for the suppression of ApoB expression is thought to result from the greater ability of the dsASO to cross the nuclear membrane.

As a result, the inventors conceived of using a double-stranded nucleic acid agent to deliver antisense oligonucleotide to a nucleus in order to improve the (therapeutic) efficacy of an ASO.

Certain embodiments relate to a double-stranded nucleic acid having an activity of modulating RNA processing by means of an antisense effect. In certain embodiments, the following are provided.

(1) A method for changing the function of a coding or non-coding RNA comprising contacting with a cell a double-stranded nucleic acid complex comprising:
a first nucleic acid strand annealed to a second nucleic acid strand, wherein:
the first nucleic acid strand comprises (i) nucleotides independently selected from natural DNA nucleotides, modified DNA nucleotides, and nucleotide analogs, (ii) no regions that have 4 or more consecutive natural DNA nucleotides, (iii) the total number of natural DNA nucleotides, modified DNA nucleotides, and nucleotide analogs in the first nucleic acid strand is from 8 to 100, and (iv) the first nucleic acid strand is capable of hybridizing to RNA inside of the cell; and
the second nucleic acid strand comprises nucleotides independently selected from natural RNA nucleotides, modified RNA nucleotides, and nucleotide analogs.

(2) The method of item (1), wherein the first nucleic acid strand comprises at least one region consisting of 2 or 3 consecutive natural DNA nucleotides.

(3) The method of item (2), wherein the first nucleic acid strand comprises a bridged nucleotide/DNA mixmer oligonucleotide.

(4) The method of item (2) or (3), wherein the bridged nucleotides are independently selected from LNA, cEt-BNA, amideBNA (AmNA), and cMOE-BNA.

(5) The method of any one of items (1)-(4), wherein at least one of the natural or one of the nucleotide analogs in the first nucleic acid strand is phosphorothioated.
(6) A method for changing the function of a coding or non-coding RNA comprising:
  contacting with a cell a double-stranded nucleic acid complex comprising:
  a first nucleic acid strand annealed to a second nucleic acid strand, wherein:
    the first nucleic acid strand is (i) selected from a morpholino oligonucleotide, a 2'-O-methyl modified oligonucleotide, a 2'-O-(2-methoxyethyl)modified oligonucleotide, or a bridged nucleotide oligonucleotide, (ii) the total number of nucleotides in the first nucleic acid strand is from 8 to 100, and (iv) the first nucleic acid strand is capable of hybridizing to RNA inside of the cell; and
    the second nucleic acid strand comprises nucleotides independently selected from natural RNA nucleotides, modified RNA nucleotides, and nucleotide analogs.
(7) The method of item (6), wherein at least one of the nucleotides in the first nucleic acid strand is phosphorothioated.
(8) The method of any one of items (1)-(7), wherein the second nucleic acid strand comprises at least one modified RNA nucleotide that has a 2'-O-methyl group and at least one internucleotide linkage at the 3' and at the 5' end of the therapeutic oligonucleotide region is more nuclease-resistant than a natural internucleotide linkage.
(9) The method of any one of items (1)-(8), wherein the second nucleic acid strand comprises a 3' wing region and a 5' wing region.
(10) The method of item (8) or (9), wherein the second nucleic acid strand comprises one or more phosphorothioated nucleotides located at both the 5' and the 3' terminal.
(11) The method of item (9) or (10), wherein the 3' wing region and the 5' wing region of the second nucleic acid strand each comprise at least one nucleotide which has a 2'-O-methyl group.
(12) The method of any of items (1)-(11), wherein the first nucleic acid strand and/or the second nucleic acid strand further comprises a functional moiety having a function selected from a labeling function, a purification function, and a targeted delivery function.
(13) The method of any of items (1)-(12), wherein the double stranded nucleic acid complex further comprises a third nucleic acid strand annealed to the first nucleic acid strand or the second nucleic acid strand.
(14) The method according to item (13), wherein the third nucleic acid strand comprises PNA nucleotides.
(15) The method according to item (13) or (14), wherein the third nucleic acid strand further comprises a functional moiety having a function selected from a labeling function, a purification function, and a targeted delivery function.
(16) The method according to item (15), wherein the functional molecule is a peptide or protein selected from a receptor ligand and an antibody.
(17) The method according to item (16), wherein the functional molecule is independently selected from P007 and B peptide.
(18) A method for modulating the processing of an RNA in a human comprising administering the double-stranded nucleic acid complex of any one of items (1)-(17) and a pharmaceutically acceptable carrier.

In further certain embodiments, the following are provided.
(1) A pharmaceutical composition for changing the function of a coding or non-coding RNA in a cell comprising:
  a double-stranded nucleic acid complex comprising:
  a first nucleic acid strand annealed to a second nucleic acid strand, wherein:
    the first nucleic acid strand comprises (i) nucleotides independently selected from natural nucleotides, modified nucleotides, and nucleotide analogs, (ii) the total number of natural nucleotides, modified nucleotides, and nucleotide analogs in the first nucleic acid strand is from 8 to 100, and (iii) the first nucleic acid strand is capable of hybridizing to RNA inside of the cell; and
    the second nucleic acid strand comprises nucleotides independently selected from natural RNA nucleotides, modified RNA nucleotides, and nucleotide analogs.
(2) The pharmaceutical composition of item 1, wherein the function is a modulation in the process of an RNA and the first nucleic acid strand comprises no regions that have 4 or more consecutive natural DNA nucleotides.
(3) The pharmaceutical composition of item 2, wherein the function of a coding or non-coding RNA is changed by inducing exon skipping.
(4) The pharmaceutical composition of item 3, wherein the first nucleic acid strand comprises at least one region consisting of 2 or 3 consecutive natural DNA nucleotides.
(5) The pharmaceutical composition of item 4, wherein the first nucleic acid strand comprises a bridged nucleotide/DNA mixmer oligonucleotide.
(6) The pharmaceutical composition of item 1, wherein the function is a modulation in the process of an RNA and the first nucleic acid strand comprises nucleotides independently selected from a morpholino oligonucleotide, a 2'-O-methyl modified oligonucleotide, a 2'-O-(2-methoxyethyl)modified oligonucleotide, or a bridged nucleotide oligonucleotide.
(7) The pharmaceutical composition of item 6, wherein the function of a coding or non-coding RNA is changed by inducing exon skipping.
(8) The pharmaceutical composition of item 1, wherein the first nucleic acid strand comprises 4 or more consecutive natural DNA nucleotide.
(9) The pharmaceutical composition of item 8, wherein the function is reducing the level of a transcription product and the first nucleic acid strand is capable of hybridizing to a non-coding region of a precursor mRNA inside of the cell.
(10) The pharmaceutical composition of item 9, wherein the first nucleic acid strand comprises a bridged nucleotide/DNA gapmer oligonucleotide.
(11) The pharmaceutical composition of any one of items 1 to 10, wherein the total number of natural DNA nucleotides, modified DNA nucleotides, and nucleotide analogs in the first nucleic acid strand is from 10 to 35.
(12) The pharmaceutical composition of item 5 or 10, wherein the bridged nucleotides are independently selected from LNA, cEt-BNA, amideBNA (AmNA), and cMOE-BNA.

(13) The pharmaceutical composition of item 5 or 10, wherein the first nucleic acid strand comprises bridged nucleotides independently selected from a nucleotide in which the carbon atom at the 2'-position and the carbon atom at the 4'-position are bridged by 4'-$(CH_2)_p$—O-2', 4'-$(CH_2)_p$—$CH_2$-2', 4'-$(CH_2)_p$—S-2', 4'-$(CH_2)_p$—OCO-2', 4'-$(CH_2)_n$—N($R_3$)—O—$(CH_2)_m$-2', where p, m and n represent an integer from 1 to 4, an integer from 0 to 2, and an integer from 1 to 3, respectively, and $R_3$ represents a hydrogen atom, an alkyl group, an alkenyl group, a cycloalkyl group, an aryl group, an aralkyl group, an acyl group, a sulfonyl group, a fluorescent or chemiluminescent label, a functional group with nucleic acid cleavage activity, or an intracellular or intranuclear localization signal peptide.

(14) The pharmaceutical composition of any one of items 1 to 12, wherein at least one of the modified nucleotides or one of the nucleotide analogs in the first nucleic acid strand is phosphorothioated.

(15) The pharmaceutical composition of any of items 1 to 14, wherein the first nucleic acid strand and/or the second nucleic acid strand further comprises a functional moiety having a function selected from a labeling function, a purification function, and a targeted delivery function.

(16) The pharmaceutical composition according to item 15, wherein said functional moiety is a molecule selected from a lipid, a sugar, a peptide, and a protein.

(17) The pharmaceutical composition according to item 16, wherein the functional moiety is joined to the 3'-terminal nucleotide and/or the 5'-terminal nucleotide of the first, second, or third nucleic acid strand.

(18) The pharmaceutical composition according to item 17, wherein the functional molecule is a peptide or protein selected from a receptor ligand and an antibody.

(19) The pharmaceutical composition according to item 18, wherein the functional molecule is independently selected from P007 and B peptide.

According to certain embodiments, an antisense nucleic acid can be delivered in a double-stranded complex and the expression or processing of a target gene, RNA, or protein can be selectively and very effectively suppressed, changed, modified, or altered by the antisense nucleic acid. In some embodiments, the double-stranded complex can be delivered to a target site with high specificity and high efficiency by associating a delivery moiety with the complex. In some embodiments, the antisense nucleic acid can be delivered to a cell nucleus with high efficiency.

Advantageous Effects of Invention

Using a double-stranded nucleic acid complex according to embodiments the present invention, in some embodiments an antisense nucleic acid can be delivered to a cell, and the expression of a target gene or the processing of pre-mRNA can be altered with high efficiency. Therefore, the double-stranded nucleic acid is useful as a pharmaceutical composition or the like for treating and preventing diseases that are associated with genetic defects, defective RNA transcripts, abnormal expression levels of genes or RNA, such as genetic diseases, metabolic diseases, tumors, and infections and/or increased level of a transcription product.

BRIEF DESCRIPTION OF DRAWINGS

FIG. 1 is a diagram illustrating the general mechanisms of certain antisense methods. As illustrated in the diagram, when an oligonucleotide (antisense oligonucleotide (ASO)) ("DNA" in the diagram) that is complementary to a partial sequence of the mRNA of a target gene is introduced into a cell, the expression of a protein that is encoded by the target gene is selectively inhibited. In the dashed box, a degradation mechanism is shown in which RNase H cleaves mRNA at a location at which it is hybridized to an ASO. As a result of RNase H cleavage, the mRNA generally will not be translated to produce a functional gene expression product.

FIG. 2 is a schematic diagram comparing the RNA product resulting from normal exon splicing versus a splice-switched RNA product caused by an antisense oligonucleotide probe.

FIG. 3 is a schematic diagram illustrating the structures of RNA, DNA, and an LNA nucleotide.

FIG. 4 shows the results of the experiments described in Example 1.

FIG. 5 shows the structural formula of various natural and modified nucleotides or nucleotide analogues.

FIGS. 6A-6B are schematic diagrams illustrating examples of suitable embodiments of double-stranded nucleic acid complexes. "X" represents a functional moiety, and may independently represent a lipid (for example, cholesterol or tocopherol), a sugar or the like, or a protein, a peptide (for example, an antibody, a cell-delivery agent) or the like.

FIGS. 7A-7B are schematic diagrams illustrating examples of suitable embodiments of a double-stranded nucleic acid complexes that contain three strands: a first ASO mixmer nucleic acid strand and a second complementary nucleic acid strand, that have different strand lengths, and a third nucleic acid strand to which is bound a functional moeity "X."

FIGS. 8A-8C are schematic illustrations of the dystrophin gene fragment expression plasmid (8A), and the structures of two double-stranded nucleic acid agents (8B, 8C) used in Example 2.

FIG. 9 shows the results of the experiments described in Example 2 comparing the exon-skipping effect of double-stranded antisense oligonucleotides according to certain embodiments.

FIG. 10 shows the results of the experiments described in Example 2 comparing the exon-skipping effect of double-stranded antisense oligonucleotides according to certain embodiments.

FIG. 11 shows the results of the experiments described in Example 2 comparing the exon-skipping effect of double-stranded antisense oligonucleotides according to certain embodiments.

FIG. 12 shows the results of the experiments described in Example 2 comparing the exon-skipping effect of double-stranded antisense oligonucleotides according to certain embodiments.

FIG. 13 shows the exon skipping activity and $T_m$ values of 15-mer double stranded SSOs.

DESCRIPTION OF EMBODIMENTS

Certain embodiments include a purified or isolated double-stranded nucleic acid complex comprising a first nucleic acid annealed to a second nucleic acid. When the complex is contacted with a cell, the complex ultimately causes changes in the expression of a target gene. Without being bound by theory, in some instances the changes are caused by altering the processing of pre-mRNA, such that the mRNA produced differs in structure or concentration from that in an untreated cell.

The double-stranded nucleic acid can change the function of a coding or non-coding RNA. The change of the function of a coding or non-coding RNA includes the modulation of RNA in the process of an RNA. The modulation of RNA includes RNA processing such as exon skipping, exon inclusion and exon retention. Further, the modulation of RNA includes block RNA expression and RNA-protein block.

In some embodiments, the first nucleic acid strand comprises (i) nucleotides independently selected from natural DNA nucleotides, modified DNA nucleotides, and nucleotide analogs, (ii) no regions that have 4 or more consecutive natural DNA nucleotides, (iii) the total number of natural DNA nucleotides, modified DNA nucleotides, and nucleotide analogs in the first nucleic acid strand is from 8 to 100, and (iv) the first nucleic acid strand is capable of hybridizing to RNA inside of the cell; and the second nucleic acid strand comprises nucleotides independently selected from natural RNA nucleotides, modified RNA nucleotides, and nucleotide analogs.

In some other embodiments, the first nucleic acid strand is (i) selected from a morpholino oligonucleotide, a 2'-O-methyl modified oligonucleotide, a 2'-O-(2-methoxyethyl) modified oligonucleotide, or a bridged nucleotide oligonucleotide, (ii) the total number of nucleotides in the first nucleic acid strand is from 8 to 100, and (iv) the first nucleic acid strand is capable of hybridizing to RNA inside of the cell; and
  the second nucleic acid strand comprises nucleotides independently selected from natural RNA nucleotides, modified RNA nucleotides, and nucleotide analogs.

In some embodiments, the double-stranded nucleic acid complex may further comprise a third nucleic acid strand. A third nucleic acid strand may anneal with either the first or with the second nucleic acid.

Some methods embodying the invention provide methods for changing the structure or concentration of mRNA in a cell comprising contacting with a cell a double-stranded nucleic acid complex comprising a first nucleic strand and a second nucleic strand having a structure according to the embodiments of the invention. Some methods can be used for changing the function of a coding or non-coding RNA, changing the splice variant resulting from pre-mRNA processing, and/or changing the sequence of a protein that is ultimately produced from the targeted gene.

The "antisense effect" means suppressing the expression of a target gene or the level of a targeted transcription product, which occurs as a result of hybridization of the targeted transcription product (RNA sense strand) with, for example, a DNA strand, or more generally strand designed to cause the antisense effect, complementary to a partial sequence of the transcription product or the like, wherein in certain instances inhibition of translation or a splicing function modifying effect such as exon skipping (see the Description in the upper part outside the area surrounded by dotted lines in FIG. 1 and in FIG. 2) may be caused by hybridization of an antisense oligonucleotide (e.g., the first strand) to a transcription product, and/or decomposition of the transcription product may occur as a result of recognition of the hybridized portion (see the Description within the area surrounded by dotted lines in FIG. 1). The oligonucleotide which can change a splicing function modifying effect is called splicing switching oligonucleotide (SSO). Further, the antisense effect is brought by targeting intron of pre-mRNA.

The "target gene" or "targeted transcription product" whose expression is suppressed, altered, or otherwise modified by the antisense effect is not particularly limited, and examples thereof include genes whose expression is increased in various diseases. Also, the "transcription product of the target gene" is a mRNA transcribed from the genomic DNA that encodes the target gene, and also includes a mRNA that has not been subjected to base modification, a mRNA precursor that has not been processed, and the like. More generally, the "transcription product" may be any RNA synthesized by a DNA-dependent RNA polymerase.

The term "purified or isolated double-stranded nucleic acid complex" as used herein means a nucleic acid complex that comprises at least one nucleic strand that does not occur in nature, or is essentially free of naturally occurring nucleic acid materials.

The term "complementary" as used herein means a relationship in which so-called Watson-Crick base pairs (natural type base pair) or non-Watson-Crick base pairs (Hoogsteen base pairs and the like) can be formed via hydrogen bonding. It is not necessary that the base sequence of the targeted transcription product, e.g., the transcription product of a target gene, and the base sequence of the first nucleic acid strand be perfectly complementary, and it is acceptable if the base sequences have a complementary of at least 70% or higher, preferably 80% or higher, and more preferably 90% or higher (for example, 95%, 96%, 97%, 98%, or 99% or higher). The complementary of sequences can be determined by using a BLAST program or the like. A first strand can be "annealed" to a second strand when the sequences are complementary. A person of ordinary skill in the art can readily determine the conditions (temperature, salt concentration, etc.) under which two strands can be annealed. Also, a person having ordinary skill in the art can easily design an antisense nucleic acid complementary to the targeted transcription product based on the information of the base sequence of, e.g., the target gene.

The first nucleic acid strand according to certain embodiments is an antisense nucleic acid that has a sequence complementary to a transcription product, such as that of a target gene.

In some embodiments, the first strand comprises nucleotides independently selected from natural DNA nucleotides, modified DNA nucleotides, and nucleotide analogs. The first strand may comprise any combination of natural or modified DNA nucleotides or nucleotide analogs, subject to the restriction that, if natural DNA nucleotides are present, no more than 1, 2, or 3 natural DNA nucleotides appear consecutively. That is, no region or segment of the first strand contains 4 or more consecutive natural DNA nucleotides.

One embodiment of the nucleotide composition of the first nucleic strand is a "mixmer." In some embodiments the mixmer comprises natural DNA nucleotides and nucleotide analogues. The nucleotide analogues may be, for example, bridged nucleotides, such as LNA nucleotides. A mixmer sequence is understood by those of skill in art, and generally includes periodic or random segment lengths of alternating types of nucleotides. As noted above, as disclosed herein, where the first strand is a mixmer no more than 1, 2, or 3 natural DNA nucleotides appear consecutively. Otherwise, there is no restriction on the ordering or arrangement of nucleotides. A mixmer is not necessarily restricted to comprising just two species of nucleotides, but may include any number of species of nucleotides (whether natural or modified nucleotides, or nucleotide analogues). For example, the first strand may comprise natural DNA nucleotides, a species of a modified nucleotide, and a species of a nucleotide analogue; or it may comprise natural DNA nucleotides and two species of nucleotide analogues.

The first nucleic acid strand comprises no region that have 4 or more consecutive natural DNA nucleotides, and includes the first nucleic acid strand which has no natural DNA nucleotides. This first nucleic acid strand comprises modified DNA nucleotides. In the present invention, the first nucleic acid strand which includes the first nucleic acid strand comprises no region that have 4 or more consecutive natural DNA nucleotides and the mixmer may be called "non-gapmer". That is, the non-gapmer is the first nucleic acid strand in which no region or segment of the first strand contains 4 or more consecutive natural DNA nucleotides.

One embodiment of the nucleotide composition of the first nucleic strand is a "gapmer". In some embodiments, the first nucleic acid strand may be arranged to have a center region consisting of at least 4 consecutive DNA nucleotides, a first 5'-wing region comprising at least two nucleotide analogs located on 5' terminal side of the central region, and a first 3'-wing region at least two nucleotide analogs located on 3' terminal side of the region as described with respect to the antisense strand in PCT/JP2012/083180, entitled "Chimeric Double-Stranded Nucleic Acid," which is incorporated herein by reference in its entirety. One embodiment of the nucleotide composition of the first nucleic strand is a homonucleotide. In such embodiments the strand comprises a single species of modified DNA nucleotide or nucleotide analogue. Examples include oligonucleotides that are prepared from morpholine nucleotides, 2'-O-methyl modified nucleotides, 2'-O-(2-methoxyethyl modified nucleotides, or from bridged nucleotides, such as LNA and other BNA's as described herein.

The strand length of the first nucleic acid strand is not particularly limited, but the strand length is usually at least 8 nucleotide bases, at least 10 bases, at least 12 bases, or at least 13 bases. The strand length may be up to 20 bases, 25 bases, or 35 bases. The strand length may even be as long as about 100 bases. Ranges of the length may be 10 to 35 bases, 12 to 25 bases, or 13 to 20 bases. In certain instances, the choice of length generally depends on a balance of the strength of the antisense effect with the specificity of the nucleic acid strand for the target, among other factors such as cost, synthetic yield, and the like.

As used herein, the term "nucleic acid" may refer to a monomeric nucleotide or nucleoside, or may mean an oligonucleotide consisting of plural monomers. The term "nucleic acid strand" or "strand" is also used herein to refer to an oligonucleotide. Nucleic acid strands may be prepared in whole or in part by chemical synthesis methods, including using an automated synthesizer or by enzymatic processes, including but not limited to polymerase, ligase, or restriction reactions.

As used herein, "DNA nucleotide" may refer to a "natural DNA nucleotide" or to a "modified DNA nucleotide." A natural DNA nucleotide is the naturally occurring base, sugar, and phosphate structure. A modified DNA nucleotide means a nucleotide unit in which the natural base, sugar, or phosphate linkage subunit is chemically modified. A modified base, sugar, or phosphate linkage subunit is one in which a single substituent has been added or substituted in a subunit, and the subunit as a whole has not been replaced with a different chemical group.

Where it is desired that a portion or the entirety of the first nucleic acid strand have high resistance to nuclease enzymes such as deoxyribonuclease and the like, the DNA nucleotide may be a modified DNA nucleotide. Examples of modified DNA nucleotides include 5-methylation, 5-fluorination, 5-bromination, 5-iodination, and N4-methylation of cytosine; 5-demethylation, 5-fluorination, 5-bromination, and 5-iodination of thymidine; N6-methylation and 8-bromination of adenine; N2-methylation and 8-bromination of guanine; phosphorothioation, methylphosphonation, methylthiophosphonation, chiral methylphosphonation, phosphorodithioation, phosphoroamidation, 2'-O-methylation, 2'-methoxyethyl(MOE)ation, 2'-aminopropyl(AP)ation, and 2'-fluorination of a natural DNA nucleotide. An embodiment of a modified DNA nucleotide having excellent pharmacokinetics is a phosphorothioated DNA nucleotide. The first strand may be phosphorothioated in one, several, or in all positions. In some embodiments one or several positions at each end of the strand are phosphorothioated. Generally, modification may be carried out such that nucleotides in the same strand may be independently subjected to different modifications. And, as discussed below, RNA nucleotides may be modified to achieve a similar effect.

In certain instances, the number of modified DNA nucleotides and the position of modification may affect the antisense effect and the like provided by the double-stranded nucleic acid complexes. The choice of modification may vary with the sequence of the target gene and the like, but a person having ordinary skill in the art can determine suitable embodiments by referring to the Descriptions of documents related to antisense methods. Furthermore, when the antisense effect possessed by a double-stranded nucleic acid complex after modification is measured, if the measured value thus obtained is not significantly lower than the measured value of the double-stranded nucleic acid complex before modification (for example, if the measured value obtained after modification is lower by 30% or more than the measured value of the double-stranded nucleic acid complex before modification), the relevant modification can be evaluated. The measurement of the antisense effect can be carried out, as indicated in the Examples below, by introducing a nucleic acid compound under test into a cell or the like, and measuring the amount of expression (amount of mRNA, amount of cDNA, amount of a protein, or the like) of the target gene in the cell in which the expression is suppressed by the antisense effect provided by the candidate nucleic acid complex being tested, by appropriately using known techniques such as Northern Blotting, quantitative PCR, and Western Blotting.

As used herein, "nucleotide analog" means a non-naturally occurring nucleotide, wherein the base, sugar, or phosphate linkage subunit has more than one substituent added or substituted in a subunit, or that the subunit as a whole has been replaced with a different chemical group. An example of an analog with more than one substitution is a bridged nucleic acid, wherein a bridging unit has been added by virtue of two substitutions on the sugar ring, typically linked to the 2' and 4' carbon atoms. In regard to the first nucleic acid strand according to certain embodiments, from the viewpoint of increasing the affinity to a partial sequence of the transcription product of the target gene and/or the resistance of the target gene to a nuclease, the first nucleic acid strand further comprises a nucleotide analog. The "nucleotide analog" may be any nucleic acid in which, owing to the modifications (bridging groups, substituents, etc.), the affinity to a partial sequence of the transcription product of the target gene and/or the resistance of the nucleic acid to a nuclease is enhanced, and examples thereof include nucleic acids that are disclosed to be suitable for use in antisense methods, in JP 10-304889 A, WO 2005/021570, JP 10-195098 A, JP 2002-521310 W, WO 2007/143315, WO 2008/043753, WO 2008/029619, and WO 2008/049085

(hereinafter, these documents will be referred to as "documents related to antisense methods"). That is, examples thereof include the nucleic acids disclosed in the documents described above: a hexitol nucleic acid (HNA), a cyclohexane nucleic acid (CeNA), a peptide nucleic acid (PNA), a glycol nucleic acid (GNA), a threose nucleic acid (TNA), a morpholino nucleic acid, a tricyclo-DNA (tcDNA), a 2'-O-methylated nucleic acid, a 2'-MOE (2'-O-methoxyethyl)lated nucleic acid, a 2'-AP (2'-O-aminopropyl)lated nucleic acid, a 2'-fluorinated nucleic acid, a 2'-F-arabinonucleic acid (2'-F-ANA), and a bridged nucleic acid (BNA).

The BNA according to certain embodiments may be any ribonucleotide or deoxyribonucleotide in which the 2' carbon atom and 4' carbon atom are bridged by two or more atoms. Examples of bridged nucleic acids are known to those of skill in the art. One subgroup of such BNA's can be described as having the carbon atom at the 2'-position and the carbon atom at the 4'-position bridged by 4'-$(CH_2)_p$—O-2', 4'-$(CH_2)_p$—$CH_2$-2', 4'-$(CH_2)_p$—S-2', 4'-$(CH_2)_p$—OCO-2', 4'-$(CH_2)_n$—$N(R_3)$—O—$(CH_2)_m$-2' (here, p, m and n represent an integer from 1 to 4, an integer from 0 to 2, and an integer from 1 to 3, respectively; and $R_3$ represents a hydrogen atom, an alkyl group, an alkenyl group, a cycloalkyl group, an aryl group, an aralkyl group, an acyl group, a sulfonyl group, and a unit substituent (a fluorescent or chemiluminescent labeling molecule, a functional group having nucleic acid cleavage activity, an intracellular or intranuclear localization signal peptide, or the like)). Furthermore, in regard to the BNA according certain embodiments, in the $OR_2$ substituent on the carbon atom at the 3'-position and the $OR_1$ substituent on the carbon atom at the 5'-position, $R_1$ and $R_2$ are typically hydrogen atoms, but may be identical with or different from each other, and may also be a protective group of a hydroxyl group for nucleic acid synthesis, an alkyl group, an alkenyl group, a cycloalkyl group, an aryl group, an aralkyl group, an acyl group, a sulfonyl group, a silyl group, a phosphoric acid group, a phosphoric acid group protected by a protective group for nucleic acid synthesis, or —$P(R_4)R_5$ (here, $R_4$ and $R_5$, which may be identical with or different from each other, each represent a hydroxyl group, a hydroxyl group protected by a protective group for nucleic acid synthesis, a mercapto group, a mercapto group protected by a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms). Non-limiting examples of such a BNA include alpha-L-methyleneoxy(4'-$CH_2$—O-2')BNA or beta-D-methyleneoxy(4'-$CH_2$—O-2')BNA, which are also known as LNA (Locked Nucleic Acid (registered trademark), 2',4'-BNA), ethyleneoxy(4'-$(CH_2)_2$—O-2')BNA which is also known as ENA, beta-D-thio(4'-$CH_2$—S-2')BNA, aminooxy(4'-$CH_2$—O—$N(R_3)$-2')BNA, oxyamino (4'-$CH_2$—$N(R_3)$—O-2')BNA which is also known as 2',4'-$BNA^{NC}$, 2',4'-$BNA^{COC}$, 3'-amino-2',4'-BNA, 5'-methyl BNA, (4'-$CH(CH_3)$—O-2')BNA, which is also known as cEt BNA, (4'-$CH(CH_2OCH_3)$—O-2')BNA, which is also known as cMOE BNA, amideBNA (4'-C(O)—N(R)-2')BNA (R=H, Me), which is also known as AmNA, and other BNA's known to those of skill in the art.

Furthermore, in the nucleotide analog, according to certain embodiments, a base moiety may be modified. Examples of the modification at a base moiety include 5-methylation, 5-fluorination, 5-bromination, 5-iodination, and N4-methylation of cytosine; 5-demethylation, 5-fluorination, 5-bromination, and 5-iodination of thymidine; N6-methylation and 8-bromination of adenine; and N2-methylation and 8-bromination of guanine. Furthermore, in the modified nucleic acid according to certain embodiments, a phosphoric acid diester binding site may be modified. Examples of the modification of the phosphoric acid diester binding site include phosphorothioation, methylphosphonation, methylthiophosphonation, chiral methylphosphonation, phosphorodithioation, and phosphoroamidation. However, from the viewpoint of having excellent pharmacokinetics, phosphorothioation may be used. The first strand may be phosphorothioated in one, several, or in all positions. In some embodiments one or several positions at each end of the strand are phosphorothioated. Generally, such modification of a base moiety or modification of a phosphoric acid diester binding site may be carried out such that the same nucleic acid may be subjected to plural kinds of modifications in combination.

Generally, modified nucleotides and nucleotide analogs are not limited to those exemplified herein. Numerous modified nucleotides and nucleotide analogs are known in art, such as, for example those disclosed in U.S. Pat. No. 8,299,039 to Tachas et al., particularly at col. 17-22, and may be used in the embodiments of this application. Examples of a natural nucleotides, modified nucleotides, and nucleotide analogs are shown in FIG. 5.

A person having ordinary skill in the art can appropriately select and use a modified nucleotide and/or nucleotide analog while taking consideration of the antisense effect, affinity to a partial sequence of the transcription product of the target gene, resistance to a nuclease, and the like. In some embodiments, the nucleotide analog is a LNA represented by the following formula (1):

Chemical Formula 1

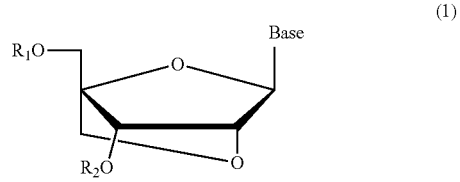

(1)

In formula (1), "Base" represents an aromatic heterocyclic group or aromatic hydrocarbon ring group which may be substituted, for example, a base moiety (purine base or pyrimidine base) of a natural nucleoside, or a base moiety of a non-natural (modified) nucleoside, while examples of modification of the base moiety include those described above; and $R_1$ and $R_2$, which may be identical with or different from each other, each represent a hydrogen atom, a protective group of a hydroxyl group for nucleic acid synthesis, an alkyl group, an alkenyl group, a cycloalkyl group, an aryl group, an aralkyl group, an acyl group, a sulfonyl group, a silyl group, a phosphoric acid group, a phosphoric acid group protected by a protective group for nucleic acid synthesis, or —$P(R_4)R_5$ {here, $R_4$ and $R_5$, which may be identical or different from each other, each represent a hydroxyl group, a hydroxyl group protected by a protective group for nucleic acid synthesis, a mercapto group, a mercapto group protected by a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms.

The compounds shown by the above chemical formulas are represented as nucleosides, but the "LNA" and more generally, the BNA according to certain embodiments include nucleotide forms in which a phosphoric acid derived group is bound to the relevant nucleoside (nucleotide). In other words, BNA's, such as LNA, are incorporated as nucleotides in the nucleic strands that comprise the double stranded nucleic acid complex.

The second nucleic acid strand according to some embodiments is a nucleic acid complementary to and capable of annealing with the first nucleic acid strand described above. It is not necessary that the base sequence of the second nucleic acid strand and the base sequence of the first nucleic acid strand be perfectly complementary to each other, and the base sequences may have a complementary of at least 70% or higher, preferably 80% or higher, and more preferably 90% or higher (for example, 95%, 96%, 97%, 98%, 99% or higher).

The second nucleic acid strand is an oligonucleotide comprising nucleotides independently selected from natural RNA nucleotides, modified RNA nucleotides, and nucleotide analogs. In some embodiments the second strand may comprise PNA nucleotides.

As used herein, "RNA nucleotide" may mean a natural RNA nucleotide or a modified RNA nucleotide wherein a modified base, sugar, or phosphate linkage subunit is chemically modified. A modified base, sugar, or phosphate linkage subunit is one in which a single substituent has been added or substituted in a subunit, and the subunit as a whole has not been replaced with a different chemical group.

Where it is desired that a portion or the entirety of the second nucleic acid strand have high resistance to a nuclease such as a ribonuclease (RNase), the RNA nucleotide may be a modified RNA nucleotide. Examples of such modification include 5-methylation, 5-fluorination, 5-bromination, 5-iodination and N4-methylation of cytosine; 5-demethylation, 5-fluorination, 5-bromination, and 5-iodination of thymidine; N6-methylation and 8-bromination of adenine; N2-methylation and 8-bromination of guanine; phosphorothioation, methylphosphonation, methylthiophosphonation, chiral methylphosphonation, phosphorodithioation, phosphoroamidation, 2'-O-methylation, 2'-methoxyethyl(MOE)ation, 2'-aminopropyl(AP)lation, and 2'-fluorination. Also, an RNA nucleotide with a thymidine base substituted for a uracil base is also contemplated. However, from the viewpoint of having excellent pharmacokinetics, phosphorothioation is used. The second strand may be phosphorothioated in one, several, or in all positions. In some embodiments one or several positions at each end of the strand are phosphorothioated. Generally, such modification may be carried out such that nucleotides in the same strand may be independently subjected to different modifications. For example, as used in the Examples described below, the same RNA may be subjected to phosphorothioation and 2'-O-methylation in order to provide resistance to enzymatic cleavage. However, where it is expected or desired for an RNA nucleotide to be cleaved by RNase H, then only either phosphorothioation or 2'-O-methylation, or neither, can be applied.

Nucleotide analogues suitable for use in the second nucleic acid strand are the same as those described above that are suitable for use in the first nucleic acid strand.

The number and type of modified nucleotides and/or nucleotide analogues and the position of each in the second nucleic acid strand may affect the antisense effect and the like provided by the double-stranded nucleic acid complex. The choice of modification may vary with the sequence of the target gene and the like, but a person having ordinary skill in the art can determine suitable embodiments by referring to the literature for antisense methods and/or by routine experimentation.

According to certain embodiments modified RNA nucleotides include 2'-O-methylated and/or phosphorothioated RNA. In some embodiments, such modified nucleotides are located at or near the 3'-terminal and/or the 5'-terminal of the second strand.

In some embodiments, the second strand is a gapmer. That is, the second strand comprises a central region and further comprises "a 3' wing region and a 5' wing region."

Generally, the central region is comprised of natural RNA nucleotides or modified RNA nucleotides. The region disposed to the 5'-terminus of the central region (i.e., the 5' wing region) and the region disposed to the 3'-terminus of the central region (i.e., the 3' wing region) may each independently comprise at least one species of a modified RNA nucleotide and/or a nucleotide analog. Typical choices and arrangements of nucleotides for the central, 3' wing, and 5' wing regions are discussed in the literature for antisense methods and are known to those of skill in the art. The lengths of the 5' wing region and the 3' wing region are independently usually 1 to 10 bases, 1 to 7 bases, or 2 to 5 bases.

The design of the 5' wing region and the 3' wing region may affect the antisense effect and the like provided by the double-stranded nucleic acid complex in certain embodiments. The number, type, and position of modified nucleotides or nucleotide analogs for a particular embodiment may vary with the sequence, but a person having ordinary skill in the art can readily determine suitable designs for gapmer strands by referring to the literature describing antisense methods and/or by routine experimentation.

The double-stranded nucleic acid complex of the present invention has a high Tm value so that the double strand is not likely to dissociate. The preferable Tm value can be predicted from the results of Example 3 below. The double-stranded nucleic acid complex of the present invention has Tm value more than 65 degrees C., preferably more than 70 degrees C., more preferably more than 80 degrees C., and more preferably less than 90 degrees C.

In the double-stranded nucleic acid complex of certain embodiments, a functional moiety may be bonded to the second nucleic acid strand. Several exemplary embodiments are illustrated in FIGS. 6 and 7. FIGS. 6A-6B show double-stranded complexes comprising a first and a second strand. The first strand may have nucleotides arranged as a mixmer, as described above, FIG. 6A, or the first strand may be a homonucleotide-type strand, FIG. 6B. Optionally, a functional moiety "X" may be joined to one of the strands. The figures show the X moiety attached to the 5' end of the second strand, however, the functional moiety, could alternatively be joined at the 3'-end, or at a position internal to the polynucleotide. In other embodiments, the complementary strand comprises more than one functional moiety, which may be the same or different, which may be joined at a plurality of positions, and/or may be joined as a group to one position of the polynucleotide. In other embodiments the functional moiety may be joined to the first strand.

FIGS. 7A-7B show double-stranded complexes comprising a first, second, and third strand. The first strand is illustrated as a mixmer, but could also be a homonucleotide-type strand. In FIG. 7A the first and third strands can both anneal to the second strand. Alternatively, the second and third strands may anneal to the first strand, FIG. 7B. Again, a functional moiety "X" may be joined to one of the strands. The figures show the X moiety attached to the third strand, however, the functional moiety, could alternatively be joined at any position as noted above, one or more types of moieties may be independently selected, and joined separately or in clusters to the strands.

The bonding between the nucleic acid strand and the functional moiety may be direct bonding, or may be indirect bonding mediated by another material. However, in certain embodiments, it is preferable that a functional moiety be directly bonded to the second nucleic acid strand via covalent bonding, ionic bonding, hydrogen bonding or the like, and from the viewpoint that more stable bonding may be obtained, covalent bonding is more preferred.

There are no particular limitations on the structure of the "functional moiety" according to certain embodiments, provided it imparts the desired function to the double-stranded nucleic acid complex and/or the strand to which it is bound. The desired functions include a labeling function, a purification function, and a delivery function. Examples of moieties that provide a labeling function include compounds such as fluorescent proteins, luciferase, and the like. Examples of moieties that provide a purification function include compounds such as biotin, avidin, a His tag peptide, a GST tag peptide, a FLAG tag peptide, and the like.

In some embodiments, the functional moiety serves to enhance transport into a cell or into a cell nucleus. For example, certain peptide tags have been shown to enhance cellular uptake of oligonucleotides when conjugated thereto. Examples include the arginine-rich peptides P007 and B peptide, disclosed in Non-Patent Document 5 and references therein. Nuclear transport can be enhanced by conjugating a moiety such as $m_3G$-CAP (see Non-Patent Document 6) to an oligonucleotide.

Furthermore, from the viewpoint of delivering the first nucleic acid strand to a target site or target region within a body with high specificity and high efficiency, and thereby suppressing very effectively the expression of a target gene by the relevant nucleic acid, it is preferable that a molecule having an activity of delivering the double-stranded nucleic acid complex of some embodiments to a "target site" within the body, be bonded as a functional moiety to the second nucleic acid strand.

The moiety having a "targeted delivery function" may be, for example, a lipid, from the viewpoint of being capable of delivering the double-stranded nucleic acid complex of certain embodiments to the liver or the like with high specificity and high efficiency. Examples of such a lipid include lipids such as cholesterol and fatty acids (for example, vitamin E (tocopherols, tocotrienols), vitamin A, and vitamin D); lipid-soluble vitamins such as vitamin K (for example, acylcarnitine); intermediate metabolites such as acyl-CoA; glycolipids, glycerides, and derivatives thereof. However, among these, from the viewpoint of having higher safety, in certain embodiments, cholesterol and vitamin E (tocopherols and tocotrienols) are used.

Furthermore, from the viewpoint of being capable of delivering the double-stranded nucleic acid complex of certain embodiments to the brain with high specificity and high efficiency, examples of the "functional moiety" according to the certain embodiments include sugars (for example, glucose and sucrose).

Also, from the viewpoint of being capable of delivering the double-stranded nucleic acid complex of certain embodiments to various organs with high specificity and high efficiency by binding to the various proteins present on the cell surface of the various organs, examples of the "functional moiety" according to certain embodiments include peptides or proteins such as receptor ligands and antibodies and/or fragments thereof.

In regard to the double-stranded nucleic acid complex of certain embodiments, the strand length of the first nucleic acid strand and the strand length of the second nucleic acid strand may be identical or may be different. As the double-stranded nucleic acid complex of some embodiments in which the first and second nucleic acid strands have the same strand length, for example, the double-stranded nucleic acids illustrated in FIGS. 6A-6B are examples of such embodiments. This is by way of example only; when the nucleic acid complex comprises two strands they may be different.

Furthermore, wherein the first and second nucleic acid strands may have different strand lengths, in some embodiments the difference in length is great enough that the double-stranded nucleic acid complex may further comprise a third nucleic acid strand annealed to the longer of the first and second nucleic acid strands as illustrated in FIGS. 7A-7B. The third nucleic acid strand is complementary to a region of whichever is the longer of the first and second nucleic acid strands, which region is protruding relative to the other nucleic acid.

The third nucleic acid strand according to some embodiments can serve as an antisense oligonucleotide, like the first nucleic acid strand. As such, the third strand can target the same sequence or a different sequence than the first strand. Thus the structure and nucleotide composition discussed in relation to the first strand can be similarly applied to the structure and composition of the third strand. Furthermore, similar to the second nucleic acid strand, the third strand may comprise a functional moiety directly or indirectly bonded thereto. The third strand can be used for various functions, one example being serving as a delivery agent of the complex.

The third strand is an oligonucleotide comprising nucleotides independently selected from natural DNA nucleotides, modified DNA nucleotides, and nucleotide analogs, or from natural RNA nucleotides, modified RNA nucleotides, and nucleotide analogs. In some embodiments the second strand may comprise PNA nucleotides.

For example, as illustrated in FIG. 7, when a PNA is used as the third nucleic acid strand, since the PNA and a protein (amino acid) can be bonded through a peptide bond, a double-stranded nucleic acid complex of some embodiments having a functional moiety X comprising a protein or the like can be easily prepared. Furthermore, since the third strand of the double-stranded nucleic acid complex illustrated in FIG. 7A is complementary to the second strand there is no need to match the PNA to the base sequence of the target gene, thus mass production can be achieved.

Thus, some suitable exemplary embodiments of the double-stranded nucleic acid complex of some embodiments have been described, but the double-stranded nucleic acid of some embodiments is not intended to be limited to the exemplary embodiments described above. Furthermore, any person having ordinary skill in the art can produce the first nucleic acid strand, the second nucleic acid strand, and the third nucleic acid strand according to some embodiments by appropriately selecting a known method. For example, the nucleic acids according to some embodiments can be produced by designing the respective base sequences of the nucleic acids on the basis of the information of the base sequence of the targeted transcription product (or, in some cases, the base sequence of a targeted gene), synthesizing the nucleic acids by using a commercially available automated nucleic acid synthesizer (products of Applied Biosystems, Inc.; products of Beckman Coulter, Inc.; and the like), and subsequently purifying the resulting oligonucleotides by using a reverse phase column or the like. Nucleic acids produced in this manner are mixed in an appropriate buffer solution and denatured at about 90 degrees C. to 98 degrees C. for several minutes (for example, for 5 minutes), subsequently the nucleic acids are annealed at about 30 degrees C. to 70 degrees C. for about 1 to 8 hours, and thus the double-stranded nucleic acid complex of some embodiments can be produced. Preparation of the annealed double-stranded complex is not limited to such a time and temperature protocol. Conditions suitable to promote annealing of two or three strands are well known in the art. Furthermore, a double-stranded nucleic acid complex to which a functional moiety is bonded can be produced by using a nucleic acid species to which a functional moiety has been bonded in advance, and performing synthesis, purification and annealing as described above. Numerous methods for joining functional moieties to nucleic acids are well-known in the art.

The double-stranded nucleic acids of some embodiments are not intended to be limited to the exemplary embodiments described above.

Methods of using the double-stranded nucleic acid complexes described above, or the compositions comprising the nucleic complex described below, include contacting the complex or composition with a "cell." The cell may be an in vitro or in vivo collection of cells. Thus, the contacting may be performed in vitro or in vivo. The cell may be a suspension of cells, a cell culture, a tissue sample, and the like, or an animal, such as a mammal, or more particularly a human. The contacting step may include putting the complex in direct contact with a cell, in solution with a cell, or may include injecting into a cell.

The double-stranded nucleic acid complex of some embodiments can be delivered to a target site with high specificity and high efficiency and can very effectively suppress the processing of pre-mRNA, the expression of a target gene or the level of a transcription product, as will be disclosed in the Examples described below. Therefore, in some embodiments compositions which comprise a double-stranded nucleic acid complex, as described herein, as an active ingredient capable of suppressing, altering, or modifying expression or the functions of RNA in a cell by means of an antisense effect. Particularly, the double-stranded nucleic acid complex of some embodiments can give high efficacy even when administered at a low concentration, and by suppressing the distribution of the antisense nucleic acid in organs other than the delivery-targeted area, adverse side effects can be reduced. Therefore, some embodiments can also provide a pharmaceutical composition intended to treat and prevent diseases that are associated with, e.g., genetic mutations, increased expression of a target gene, such as metabolic diseases, tumors, and infections.

The composition containing the double-stranded nucleic acid complex of some embodiments can be formulated by known pharmaceutical methods. For example, the composition can be used enterally (perorally or the like) in the form of capsules, tablets, pills, liquids, powders, granules, fine granules, film-coating agents, pellets, troches, sublingual agents, peptizers, buccal preparations, pastes, syrups, suspensions, elixirs, emulsions, coating agents, ointments, plasters, cataplasms, transdermal preparations, lotions, inhalers, aerosols, injections and suppositories, or non-enterally.

In regard to the formulation of these preparations, pharmacologically acceptable carriers or carriers acceptable as food and drink, specifically sterilized water, physiological saline, vegetable oils, solvents, bases, emulsifiers, suspending agents, surfactants, pH adjusting agents, stabilizers, flavors, fragrances, excipients, vehicles, antiseptics, binders, diluents, isotonizing agents, soothing agents, extending agents, disintegrants, buffering agents, coating agents, lubricating agents, colorants, sweetening agents, thickening agents, corrigents, dissolution aids, and other additives can be appropriately incorporated.

On the occasion of formulation, as disclosed in Non-Patent Document 7, the double-stranded nucleic acid complex of some embodiments to which a lipid is bound as a functional moiety may be caused to form a complex with a lipoprotein, such as chylomicron or chylomicron remnant. Furthermore, from the viewpoint of increasing the efficiency of enteral administration, complexes (mixed micelles and emulsions) with substances having a colonic mucosal epithelial permeability enhancing action (for example, medium-chain fatty acids, long-chain unsaturated fatty acids, or derivatives thereof (salts, ester forms or ether forms)) and surfactants (nonionic surfactants and anionic surfactants) may also be used, in addition to the lipoproteins.

There are no particular limitations on the preferred form of administration of the composition of some embodiments, and examples thereof include enteral (peroral or the like) or non-enteral administration, more specifically, intravenous administration, intraarterial administration, intraperitoneal administration, subcutaneous administration, intracutaneous administration, tracheobronchial administration, rectal administration, and intramuscular administration, and administration by transfusion.

The composition of some embodiments can be used for animals including human beings as subjects. However, there are no particular limitations on the animals excluding human beings, and various domestic animals, domestic fowls, pets, experimental animals and the like can be the subjects of some embodiments.

When the composition of some embodiments is administered or ingested, the amount of administration or the amount of ingestion may be appropriately selected in accordance with the age, body weight, symptoms and health condition of the subject, type of the composition (pharmaceutical product, food and drink, or the like), and the like. However, the effective amount of ingestion of the composition according to the certain embodiments is 0.001 mg/kg/day to 50 mg/kg/day of the double stranded nucleic acid complex.

The double-stranded nucleic acid complex of some embodiments can be delivered to a target site with high specificity and high efficiency, and can suppress the expression of a target gene or the level of a transcription product very effectively, as will be disclosed in the Examples that follow. Therefore, some embodiments can provide a method of administering the double-stranded nucleic acid complex of some embodiments to a subject, and suppressing the expression of a target gene or transcription product level by means of an antisense effect. Furthermore, a method of treating or preventing various diseases that are associated with, e.g., increased expression of target genes, by administering the composition of some embodiments to a subject can also be provided.

EXAMPLES

Hereinafter, some embodiments will be described more specifically by way of Examples and Comparative Examples, but the embodiments not intended to be limited to the following Examples.

Example 1

The accessibility of a double-stranded antisense nucleic acid complex to the nucleus of Huh-7 cells was tested and compared with that of a single-stranded antisense oligonucleotide. In the experiment, to the extent the antisense oligonucleotide (ASO) is able to reach the nucleus, the ASO should be able to suppress the expression of the targeted gene, ApoB, and thus the amount of ApoB mRNA would show a corresponding decrease.

A single-stranded LNA/DNA gapmer antisense oligonucleotide (SEQ ID NO:1) and a complementary RNA-based strand (SEQ ID NO:2) were prepared with the following sequence and composition:

```
16 mer ASO (targeted to intron human
apoB mRNA):
                                 SEQ ID NO: 1
5'-C*T*C*c*c*a*c*c*a*c*a*t*a*G*C*A-3'

16 mer cRNA (targeted to intron human
apoB mRNA):
                                 SEQ ID NO: 2
5'-g*c*u*AUGUGGUGGG*a*u*g-3'
```

The small italic letters represent DNA, underlined capital types represent LNA (C denotes LNA methylcytosine), the upper case letters represent RNA, the lower case letters represent 2'-O-methyl sugar modification, and the asterisks represent phosphorothioate linkages.

A double-stranded complex (dsASO) was prepared from SEQ ID NO:1 (ASO) and 2 (cRNA) by adding equimolar amounts of the two strands to phosphate-buffered saline (PBS, Sigma-Aldrich, St. Louis, Mo.) solution, heating the solution at 95 degrees C. for 5 min and slowly cooling the solution to room temperature to form the annealed double-stranded complex.

Cell culture. Huh-7 cells were maintained in Dulbecco's modified Eagle's medium (Sigma-Aldrich) supplemented with 10% fetal bovine serum (Invitrogen, Carlsbad, Calif.), 100 U/ml penicillin, and 100 microg of streptomycin at 37 degrees C. in 5% $CO_2$.

In vitro gene silencing. The cells were transfected separately with 10 or 25 nmol/L of ASO and dsASO using Lipofectamine RNAiMAX (Invitrogen). The cells were harvested 24 h after transfection. Total RNA was extracted and the amount of endogenous apoB mRNA was measured using quantitative RT-PCR according to standard methods.

The results of the experiment comparing a Lipofectamine negative control with the double-stranded and single-stranded (conventional) ASO's are shown in FIG. 4. As is evident by the data, the single-stranded ASO showed nearly no suppression of mRNA levels compared to the negative control. In contrast, the dsASO showed 56% suppression at 10 nM and 72% suppression at 25 nM of the expressed levels of the targeted gene.

Because the Lipofectamine RNAiMAX is expected to deliver the oligonucleotides only as far as the cytosol and not across the nuclear membrane, it is suggested that there is an intracellular transfer mechanism for double-stranded complexes, but not for single-stranded oligonucleotides, from the cytosol to the nucleus.

Example 2

The ability of a double-stranded antisense nucleic acid complex according to one embodiment of the invention to cause exon-skipping during the processing of pre-mRNA of a portion of the dystrophin gene was tested and compared with that of a single-stranded antisense oligonucleotide.

For the experiment, a human dystrophin gene fragment stable expression plasmid was constructed and stable cell lines containing the construct were established. The dystrophin gene fragment has a full-length sequence from Exon 57 to Exon 59 except Intron 57, which was shortened for convenience because of its length.

Expression of the dystrophin fragment in the stable cell line would normally be expected to yield an mRNA comprising exons 57, 58, and 59. In the presence of a splice-switching oligonucleotide, which has the ability to cause the skipping of exon 58 during the processing of the pre-mRNA, however, the expressed mRNA would be expected to comprise exon 57 and 59 but to lack exon 58.

In the experiment, to the extent the antisense oligonucleotide (ASO) is able to reach the nucleus, the ASO should be able to alter the splicing of the mRNA product expressed from the dystrophin gene, and thus the amount of the three-exon fragment (exons 57, 58, and 59) of dystrophin would show a corresponding decrease.

Two different antisense oligonucleotides that can cause exon skipping of exon 58 were prepared and tested. One ASO binds to a sequence within intron 57, and the other ASO binds to a sequence within exon 58, though both cause the skipping of exon 58. Two different complementary strands were prepared for each ASO to be used to form the double-stranded antisense nucleic acid complex. In each case, the complementary strands are 2'-OMe RNA/RNA gapmers with 3' and 5' wings of either 2 bases or 3 bases, as described below.

Construction of Dystrophin Gene Expression Plasmids. A schematic of the dystrophin gene fragment plasmid is illustrated in FIG. 8A.

The starting plasmid for construction was the pcDNA5/FRT vector (Invitrogen, Carlsbad, Calif.). To generate fragment containing Flag Tag, two oligonucleotides, 5'-AGCTTACCATGGATTACAAGGACGACGACGACAAG GGGGTAC-3' (SEQ ID NO: 3)(including HindIII and KpnI site, underlined) and 5'-CCC-CTTGTCGTCGTCGTCCTT-GTAATCCATGGTA-3' (SEQ ID NO: 4) were annealed together. After annealing, the fragment was cloned into HindIII/KpnI sites of pcDNA5/FRT vector (pcDNA5/FRT-FLAG). The Flag Tag contains two silent mutations to avoid the expressions of extra first methionine accidentally.

Using the pcDNA3-EGFP vector as a template, the EGFP fragment was amplified using a forward primer 5'-CCCGGGTGTGAGCAAGGGCGAGGAGCTGT-3' (SEQ ID NO: 5) (including SmaI site, underlined) and a reverse primer 5'-ATAGGGCCCTTACTTGTACAGCTCGTC-CAT-3' (SEQ ID NO: 6) (including ApaI site, underlined). The cycling conditions were: 94 degrees C. for 2 min, then 98 degrees C. for 0.5 min, 63 degrees C. for 0.5 min, 68 degrees C. for 0.75 min for 35 cycles, and 68 degrees C. for 3 min. PCR reactions were carried out using KOD FX NEO (TOYOBO, Osaka, Japan according to the manufacturer's instructions. The EGFP fragment was inserted into SmaI/ApaI digested pcDNA5/FRT-FLAG vector (pcDNA5/FRT-FLAG-EGFP).

Using the pDsRed-Express-N1 vector as a template, the EGFP fragment was amplified using a forward primer 5'-ATAT<u>GGATCC</u>A<u>ACCGGT</u> GTGGCCTCCTCCGAG-GACGTCA-3' (SEQ ID NO: 7) (including BamHI and AgeI site, underlined) and a reverse primer 5'-CGGTCTACAG-GAACAGGTGGTGGC-3' (SEQ ID NO: 8). The cycling conditions were: 94 degrees C. for 2 min, then 98 degrees C. for 0.5 min, 63 degrees C. for 0.5 min, 68 degrees C. for 0.75 min for 35 cycles, and 68 degrees C. for 3 min. PCR reactions were carried out using KOD FX NEO (TOYOBO, Osaka, Japan) according to the manufacturer's instructions. The EGFP fragment was inserted into BamHI/SmaI digested pcDNA5/FRT-FLAG-DsRed vector (pcDNA5/FRT-FLAG-DsRed-EGFP).

To collect fluorescence proteins into nucleus, the NLS sequence (Nucleus Localized Signal) was inserted into BamHI digested pcDNA5/FRT-Flag-DsRed-EGFP. The NLS sequence was prepared by annealing two oligonucleotides 5'-ATGCCCCAAAAAAAAAACGCAAAGTG-GAGGACCCAAAGGTACCAAAG-3' (SEQ ID NO: 9) and 5'-GATCCTTTGGTACCTTTGGGTCCTCCACTTT-GCGTTTTTTTTTTGGGGCATGTAC-3' (SEQ ID NO: 10) (pcDNA5/FRT-Flag-NLS-DsRed-EGFP).

To generate human Dystrophin gene stable expression plasmids, a human Dystrophin gene fragment was obtained by means of PCR with a HepG2 genome. The plasmid which contains Dystrophin gene fragment has a full-length sequence from Exon 57 to Exon 59 except Intron 57. Intron 57 sequence (17683 base pairs) is too long for inserting into plasmid, therefore a portion of Intron 57, sequence +207 to +17486, was deleted by means of PCR using a forward primer 5'-AAC<u>GGTACC</u> AACGCTGCTGTTCTTTTCA-3' (SEQ ID NO: 11) (including KpnI site, underlined), a reverse primer 5'-GTGTTTGTAATGGACGATTTCT-TAAAGGGTATT-3' (SEQ ID NO: 12) and forward primer 5'-AAATCGTCCATTACAAACACAGCGCTTTCC-3' (SEQ ID NO: 13), reverse primer 5'-AG<u>ACCGGT</u>ACTCCTCAGCCTGCTTTCGTA-3' (SEQ ID NO: 14) (including AgeI site, underlined). The fragment was cloned into KpnI/AgeI digested pcDNA5/FRT-Flag-NLS-DsRed-EGFP vector (pcDNA5/FRT-Flag-NLS-DMD-Exon57_58_59(short-Intron57)-DsRed-EGFP).

All constructs were verified by ABI PRISM 310 Analyzer (Applied Biosystems, Foster City, Calif., USA) or sequencing by Fasmac (Kanagawa, Japan).

Stable Cell Line Establishment. Flp-In-293 (Invitrogen, Carlsbad, Calif.) cells were cultured in Dulbecco's Modified Eagle's Medium (DMEM) (Nacalaitesque, Kyoto, Japan) supplemented with 10% fetal bovine serum containing 10% fetal bovine serum (FBS) (Biowest, Nuaille, France), 2% Penicillin-Streptomycin Mixed Solution (Penicillin 10,000 units/mL, Streptomycin 10,000 microg/mL) (Nacalaitesque, Kyoto, Japan) and selected with 100 mg/mL Zeocin at 37 degrees C. The pcDNA5/FRT-Flag-Dys57>59di-NLS-DsRed-EGFP and pOG44 (the Flp recombinase expression plasmid) (Invitrogen, Carlsbad, Calif.) were co-transfected into the Flp-In-293 cells. Stable cell lines were selected on the basis of Hygromycin B 50 mg/mL (Invitrogen, Carlsbad, Calif.) resistance.

Cell Culture. The stable cell line was cultured in Dulbecco's Modified Eagle's Medium (DMEM) (Nacalaitesque, Kyoto, Japan) containing 10% fetal bovine serum (FBS) (Biowest, Nuaille, France) and 2% Penicillin-Streptomycin Mixed Solution (Penicillin 10,000 u/mL, Streptomycin 10,000 microg/mL) (Nacalaitesque, Kyoto, Japan).

Antisense Oligonucleotides and Complementary Strands. The sequences and compositions of the nucleic acid strands used in the experiments are listed below. Oligonucleotides (ASO and cGapmers) were synthesized by Gene Design (Osaka, Japan). An illustration of the double-stranded complexes formed between ASO 2 and cGapmer(2) (SEQ ID NO: 18 and 19), and ASO 2 and cGapmer(3) (SEQ ID NO: 18 and 20) are shown in FIGS. 8B-8C.

```
ASO 1 DMDintron57-17683-BNA(15)PS
                                        SEQ ID NO: 15
5'-c*C*c*t*C*t*t*G*a*a*G*g*c*C*t-3' cGapmer(2) CSmRNA(2-2_2'OMe_PS)_DMD-
intron57-17683(15)
                                        SEQ ID NO: 16
5'-a*g*GCCUUCAAGAGg*g-3' cGapmer(3) CSmRNA(3-3_2'OMe_PS)_DMD-
intron57-17683(15)
                                        SEQ ID NO: 17
5'-a*g*g*CCUUCAAGAg*g*g-3'

ASO 2 DMD-exon58-106-BNA(15)PS
                                        SEQ ID NO: 18
5'-t*C*t*g*G*g*c*T*c*c*T*g*g*T*a-3' cGapmer(2) CSmRNA(2-2_2'OMe_PS)_DMD-
exon58-106(15)
                                        SEQ ID NO: 19
5'-u*a*CCAGGAGCCCAg*a-3' cGapmer(3) CSmRNA(3-3_2'OMe_PS)_DMD-
exon58-106(15)
                                        SEQ ID NO: 20
5'-u*a*c*CAGGAGCCCa*g*a-3'
```

The small italic letters represent DNA, underlined capital types represent LNA (C denotes LNA methylcytosine), the upper case letters represent RNA, the lower case letters represent 2'-O-methyl sugar modification, and the asterisks represent phosphorothioate linkages.

Double-stranded nucleic complexes were prepared by annealing the appropriate pair of oligonucleotides (i.e., SEQ ID NOS: 15/16; 15/17; 18/19; and 18/20). Equimolar solutions of an ASO and a complementary RNA cGapmer strand were combined in 50 mM Tris-HCl, 20 mM NaCl buffer. The solution was heated at 95 degrees C. for 5 minutes, cooled to 37 degrees C. over 60 minutes, and held at 37 degrees C. for 60 minutes.

Transfection of single-stranded and double-stranded ASOs. Stable cell lines were seeded one day before transfection at a density of $5.0 \times 10^5$ cells/well in 24-well plates. At 30-40% confluence, cells were transfected with either a single-stranded ASO or a double-stranded ASO/cGapmer complex using Lipofectamine RNAi MAX (Invitrogen, Carlsbad, Calif.) according to the manufacturer's instructions. 1.0 microL Lipofectmine RNAi MAX was used per each 10 nM ASO or cGapmer. The double-stranded complexes were tested over a range of concentrations, 3 nM, 10 nM, 30 nM, and 100 nM of ASO strand. (Final concentration: 1-20 microL/mL of Lipofectamine RNAi MAX, 6-200 nM of ASO and cGapmer). Cells were harvested 24 h post-transfection, and the total RNA was extracted.

RNA Isolation and Reverse Transcription. Total RNA samples were isolated from the cells using the QuickGene 800 (FUJI-FILM, Tokyo, Japan) with RNA cultured cell kit S (TOYOBO, Osaka, Japan) according to the manufacturer's instructions. First-strand cDNA was synthesized from 1.5 microg of total RNA of each cell sample using the Rever Tra Ace qPCR Master Mix (TOYOBO, Osaka, Japan) according to the manufacturer's instructions.

Real-Time PCR Analysis. The cDNAs were used as templates for individual PCR reactions using specific primer sets, which were designed by the Primer Express program (Applied Biosystems, Foster City, Calif., USA). The sequences of primers are shown below.

```
Exon 58 Skip analysis primers:
                                SEQ ID NO: 21
5'- TCAGCCTGCTTTCGTAGA-3'

SEQ ID NO: 22
5'- GATGTACATAGGAGCTGCCTC-3'

GAPDH analysis primers:
                                SEQ ID NO: 23
5'- GGTCACCAGGGCTGCTTTT-3'

SEQ ID NO: 24
5'- GTAAACCATGTAGTTGAGGTCAATGAAG-3'
```

All primers were synthesized by Hokkaido System Sciences (Sapporo, Japan). PCR reactions were carried out using SYBR Green Real Time PCR Master Mix (TOYOBO, Osaka, Japan) according to the manufacturer's instructions except annealing time. The annealing time was changed into 15 sec especially on Exon 58 skipping detection. The PCR analysis was performed using the Step one plus (Applied Biosystems, Foster City, Calif., USA). Amplification specificity was verified by visualizing PCR products on ethidium bromide stained 2.0% agarose gel. Glyceraldehyde-3-phosphate dehydrogenase (GAPDH) was used for normalizing each expression data.

RT-PCR Analysis. The cDNAs were used 1.0 microL as templates for individual PCR reactions using specific primer sets, which were designed by the Primer3 program written by the Whitehead Institute. All primers were synthesized by Hokkaido System Sciences (Sapporo, Japan). The sequences of primers are shown below.

```
Dystrophin primers:
                                SEQ ID NO: 25
5'- AACGGTACCAACGCTGCTGTTCTTTTTCA-3'

SEQ ID NO: 26
5'- CTTGGAGCCGTACTGGAACT-3'

GAPDH analysis primers:
                                SEQ ID NO: 27
5'- ACCACAGTCCATGCCATCAC-3'

SEQ ID NO: 28
5'- TCCACCACCCTGTTGCTGTA-3'
```

The cycling conditions were: 95 degrees C. for 1 min, then 98 degrees C. for 0.5 min, 55 degrees C. for 0.5 min, 68 degrees C. for 0.25 min for 25 cycles, and 68 degrees C. for 3 min. PCR reactions were carried out using KOD FX NEO (TOYOBO, Osaka, Japan). Reaction mixture preparations followed the manufacturer's instructions.

Experiment. To summarize, (exon-skipping) antisense oligonucleotides that target dystrophin and complementary gapmer RNA strands were prepared and annealed to form a double-stranded nucleic acid complex. The complexes were transfected using RNAiMAX to a stable cell line containing a plasmid carrying a dystrophin gene fragment (exons 57, 58, 59). Twenty-four hours after transfection, the total RNA was extracted, subjected to reverse transcription, and analyzed by real-time PCR. PCR was used to further amplify the products, and the amplicons were analysis by gel electrophoresis. From the gel, the amount of exon 58-skipping induced by each ASO was calculated. The amounts were normalized against GAPDH expression observed in the cell. The results for the double-stranded complexes were compared against the single-stranded complex alone, and against an untreated control (no oligonucleotides included in the transfection solution). All tests were performed in triplicate.

The results for the various ASO's and double-stranded complexes are graphed in FIGS. 9-12. As is apparent from the graphs, the degree of exon skipping caused by the double-stranded complexes increased with concentration of the complex. At the highest concentration (100 nM) the cells were observed to be adversely affected. Although very few cells died, the expression levels were probably affected by the dose.

In all cases, the degree of exon 58 skipping induced by the double-strand ASO complex was significantly greater than that for the single-stranded ASO at the same concentration (10 nM). Above each bar in the graphs is the value for the Dunnett's test applied to the P value for each test (N=3) relative to the ASO only control.

Therefore, it was demonstrated that a bridged nucleotide/DNA mixmer, when annealed with an RNA-based complementary strand to obtain a double-stranded nucleic acid complex, can deliver the ASO to the nucleus and induce an exon-skipping effect in the processing of pre-mRNA to a greater extent than a single-stranded ASO.

Example 3

Material and Methods

Synthesis of Splice-Switching Oligonucleotides (SSOs)

All SSOs used in this study are shown in Tables 1. The sequence of SSOs was optimized by a systematic screening as shown in the literature, Shimo. T. et al. Design and evaluation of locked nucleic acid-based splice-switching oligonucleotides in vitro, Nucleic Acids Research, doi: 10.1093/nar/gku512, in press (2014). Two types of modification, 2',4'-BNA and 2'-OMe, were incorporated into the SSO sequences, in which the phosphodiester linkages were completely replaced by phosphorothioate linkages. All SSOs were designed to have sequences complementary to human dystrophin gene and were synthesized and purified by Gene Design Inc. (Osaka, Japan).

Synthesis of Modified Complementary RNA

All modified complementary RNAs (modified cRNAs) used in this study are shown in Table 2. 2'-OMe modification was incorporated into the modified cRNA sequences, in which the phosphodiester linkages were partially replaced by phosphorothioate linkages. The modified cRNAs were synthesized and purified by Gene Design Inc.

Preparation of Double Stranded SSOs

Equimolecular amounts of single stranded SSOs and complementary RNA were dissolved in annealing buffer containing 50 mM Tris-HCl and 100 mM NaCl. The samples were boiled and followed by slow cooling to room temperature.

SSOs Transfection

Stable cell lines were seeded one day before transfection at a density of $8.0 \times 10^4$ cells/well on 24-well plates. At 30-40% confluence, SSOs were transfected into cells by using Lipofectamine RNAiMAX (Invitrogen, Carlsbad, Calif.) according to the manufacturer's instructions. After 24 h, the cells were harvested.

RNA Isolation and cDNA Synthesis

Total RNA samples were isolated from the cells using the QuickGene 800 and QuickGene RNA cultured cell kit S (KURABO, Osaka, Japan) according to the manufacturer's instructions. First strand cDNA was synthesized from 150 ng of the total RNA of each cell sample using the ReverTra Ace qPCR RT Master Mix (TOYOBO, Osaka, Japan) according to the manufacturer's instructions.

Quantitative Real-Time RT-PCR Analysis

The cDNA was used as a template for individual PCR reactions using exon skipping specific primer sets (Table 3), which were designed using the Primer Express program (Applied Biosystems, Foster City, Calif.) and Primer3 program. PCR reactions were conducted using SYBRGreen Real-time PCR Master Mix (TOYOBO) according to the manufacturer's instructions, except that the annealing time was reduced to 15 s. The quantitative PCR analysis was performed using the StepOnePlus device (Applied Biosystems). Amplification specificity was verified by visualizing the PCR products on an ethidium bromide-stained 2% agarose gel. GAPDH was used to normalize the expression data.

Ultraviolet (UV) Melting Experiment

UV melting experiments were conducted using a Shimadzu UV-1650PC UV-Vis spectrophotometer equipped with a $T_m$ analysis accessory TMSPC-8 (Shimadzu, Kyoto, Japan). Equimolecular amounts of two single stranded oligonucleotides were dissolved in 10 mM sodium phosphate buffer (pH 7.2) containing 10 mM NaCl to give a final strand concentration of 2.0 microM. The samples were boiled and followed by slow cooling to room temperature. The absorption was recorded at 260 nm in the forward and reverse direction from 5 to 95 degrees C. at a scan rate of 0.5 degrees C./min. The first derivative was calculated from the UV melting profile. The peak temperatures in the derivative curve were designated as the melting temperature, $T_m$.

SSOs used for this experiment are shown below. Eleven SSOs for dystrophin exon 58 skipping are shown. Sequences are shown from 5' to 3'.

```
ASO 3 DMDintron57-17684-1
                                 SEQ ID NO: 29
5'- T*C*C*C*T*C*T*T*G*A*A*G*G*C*C -3'

ASO 4 DMDintron57-17684-2
                                 SEQ ID NO: 30
5'- T*c*C*c*T*c*T*t*G*a*A*g*G*c*C -3'

ASO 5 DMDintron57-17684-3
                                 SEQ ID NO: 31
5'- t*C*c*C*t*C*t*T*g*A*a*G*g*C*c -3'

ASO 6 DMDintron57-17684-4
                                 SEQ ID NO: 32
5'- t*c*C*c*t*C*t*t*G*a*a*G*g*c*C -3'

ASO 7 DMDintron57-17684-5
                                 SEQ ID NO: 33
5'- t*c*C*c*t*C*t*t*g*a*a*G*g*c*C -3'
```

```
ASO 8 DMDintron57-17684-6
                                 SEQ ID NO: 34
5'- t*c*C*c*t*c*t*t*G*a*a*g*g*c*C -3'

ASO 9 DMDintron57-17684-7
                                 SEQ ID NO: 35
5'- t*c*C*c*t*c*t*t*g*a*a*g*g*c*C -3'

ASO 10 DMDintron57-17684-8
                                 SEQ ID NO: 36
5'- t*c*c*c*t*c*t*t*G*a*a*g*g*c*c -3'

ASO 11 DMDintron57-17684-9
                                 SEQ ID NO: 37
5'- u*c*c*c*u*c*u*u*g*a*a*g*g*c*c -3'

ASO 12 DMDintron57-17684-10
                                 SEQ ID NO: 38
5'- t*c*c*c*t*c*t*t*g*a*a*g*g*c*c -3'

ASO 13 DMDintron57-17684-11
                                 SEQ ID NO: 39
5'- t*c*c*c*t*c*t*t*g*a*a*g*g*c*c -3'
```

The small italic letters represent DNA, underlined capital types represent LNA (C denotes LNA methylcytosine), the lower case letters represent 2'-O-methyl sugar modification, and the asterisks represent phosphorothioate linkages.

Table 1 show the results.

TABLE 1

| Entry | ID | Sequence of SSO | $T_m$ (° C.) native cRNA[i] | $T_m$ (° C.) modified cRNA[ii] |
|---|---|---|---|---|
| 1 | DMDintron57-17684-1 | T*C*C*C*T*C*T*T*G*A*A*G*G*C*C | >95.0 | >95.0 |
| 2 | DMDintron57-17684-2 | T*c*C*c*T*c*T*t*G*a*A*g*G*c*C | 82.6 ± 2.3 | 84.4 ± 2.1 |
| 3 | DMDintron57-17684-3 | t*C*c*C*t*C*t*T*g*A*a*G*g*C*c | 84.6 ± 2.7 | 85.4 ± 2.1 |
| 4 | DMDintron57-17684-4 | t*c*C*c*t*C*t*t*G*a*a*G*g*c*C | 69.5 ± 0.5 | 72.5 ± 1.2 |
| 5 | DMDintron57-17684-5 | t*c*C*c*t*C*t*t*g*a*a*G*g*c*C | 68.8 ± 2.6 | 68.9 ± 0.6 |
| 6 | DMDintron57-17684-6 | t*c*C*c*t*c*t*t*G*a*a*g*g*c*C | 62.1 ± 1.7 | 63.7 ± 1.3 |
| 7 | DMDintron57-17684-7 | t*c*C*c*t*c*t*t*g*a*a*g*g*c*C | 57.7 ± 2.1 | 59.5 ± 2.0 |
| 8 | DMDintron57-17684-8 | t*c*c*c*t*c*t*t*G*a*a*g*g*c*c | 55.1 ± 1.5 | 55.6 ± 1.4 |
| 9 | DMDintron57-17684-9 | u*c*c*c*u*c*u*u*g*a*a*g*g*c*c | 64.9 ± 0.6 | 66.8 ± 2.0 |
| 10 | DMDintron57-17684-10 | t*c*c*c*t*c*t*t*g*a*a*g*g*c*c | 50.1 ± 1.8 | 51.8 ± 0.5 |

TABLE 1-continued

| Entry | ID | Sequence of SSO | $T_m$ (° C.) native cRNA[i] | $T_m$ (° C.) modified cRNA[ii] |
|---|---|---|---|---|
| 11 | DMDintron57-17684-11 | t*c*c*c*t*c*t*t*g*a*a*g*g*c*c | 39.9 ± 1.3 | 42.8 ± 1.8 |

$T_m$ values of the duplexes between SSO and native/modified cRNA (2 microM duplex in 10 mM phosphate buffer (pH 7.2), 10 mM NaCl (n = 3-4)) were determined with complementary native RNA and modified cRNA (+/- SD).
[i] Tm (degrees C.) of the duplex containing the native cRNA, rGGCCUU-CAAGAGGGA (SEQ ID NO: 40).
[ii] Tm (degrees C.) of the duplex containing the modified cRNA, cGapmer CSmRNA(2-2_2'OMe_PS)_DMD-intron57-17684(15).
The sequence of the modified cRNA, DMD-intron57-17684_cRNA, was shown below.
cGapmer CSmRNA(2-2_2'OMe_PS)_DMD-intron57-17684(15) SEQ ID NO: 41 5'- g*g*CCUUCAAGAGGg*a-3'

The upper case letters represent RNA, the lower case letters represent 2'-O-methyl sugar modification, and the asterisks represent phosphorothioate linkages.

Primers used for quantitative real-time RT-PCR analysis. Sequences of forward (For.) and reverse (Rev.) primer for each target are shown in Table 2. Sequences are shown from 5' to 3'. The small italic letters represent DNA.

TABLE 2

| Gene | | Sequence | Size (bp) |
|---|---|---|---|
| DMD | For. primer: | gatgtacataggagctgcctc (SEQ ID NO: 42) | 70 (Exon 57/59 junction) |
| | Rev. primer: | tcagcctgctttcgtaga (SEQ ID NO: 43) | (Exon 59) |

TABLE 2-continued

| Gene | | Sequence | Size (bp) |
|---|---|---|---|
| GAPDH | For. primer: | ggtcaccagggctgctttt (SEQ ID NO: 44) | 85 |
| | Rev. primer: | gtaaaccatgtagttgaggtcaatgaag (SEQ ID NO: 45) | |

Results

FIG. 13 shows the exon skipping activity and $T_m$ values of 15-mer double stranded SSOs.

The level of exon 58-skipped mRNA fragments were measured by quantitative real-time RT-PCR and normalized against the signal of GAPDH mRNA, relative to the value in the no treatment set as 1. Values represent the mean +/- standard deviation of triplicate samples. The $T_m$ value of each SSO with a modified complementary RNA is also shown by square symbol in FIG. 13. "#" indicates that no sigmoidal melting curve was observed. The data are the mean +/- standard deviation (n=3-4). Mock: treated with Lipofectamine only; no treatment: no transfection.

Double stranded SSOs with high $T_m$ values, DMD-intron57-17684-2, DMD-intron57-17684-3, DMD-intron57-17684-4, DMD-intron57-17684-5 and DMD-intron57-17684-9, showed high exon skipping activity.

As shown in FIG. 13, the double stranded SSOs showed the high exon skipping activity at $T_m$ value of 65 to 88 degrees C.

Sequence Listing Free Text 1-4, 6, 7, 9, 10, 15-20, 29-41 Synthetic
5, 8, 11-14, 21-28, 42-45 Primer

The invention claimed is:

1. A pharmaceutical composition for modulating exon skipping of a coding or non-coding RNA in a mammalian cell comprising:
a double-stranded nucleic acid complex comprising:
a first nucleic acid strand annealed to a second nucleic acid strand, wherein:
the first nucleic acid strand comprises (i) 8 to 100 nucleotides independently selected from natural nucleotides, modified nucleotides, and nucleotide analogs, (ii) at least one region consisting of 2 or 3 consecutive natural DNA nucleotides, (iii) no regions that have greater than 3 consecutive natural DNA nucleotides, and (iv) a bridged nucleotide/DNA mixmer oligonucleotide; and wherein the first nucleic acid strand is a splice-switching oligonucleotide (SSO) and is capable of hybridizing to the coding or non-coding RNA inside of the mammalian cell; and
the second nucleic acid strand comprises nucleotides independently selected from natural RNA nucleotides, modified RNA nucleotides, and nucleotide analogs, and at least one region comprising consecutive natural RNA nucleotides,
wherein the at least one region consisting of 2 or 3 consecutive natural DNA nucleotides of the first nucleic acid strand forms a heteroduplex with the at least one region comprising consecutive natural RNA nucleotides of the second nucleic acid strand.

2. The pharmaceutical composition of claim 1, wherein the modulation of exon skipping affects one or more of RNA processing, RNA expression or protein expression.

3. The pharmaceutical composition of claim 1, wherein the first nucleic acid strand comprises nucleotides independently selected from a morpholino oligonucleotide, a 2'-O-methyl modified oligonucleotide, a 2'-O-(2-methoxyethyl) modified oligonucleotide, or a bridged nucleotide, wherein the modulation of exon skipping affects one or more of RNA processing, RNA expression or protein expression.

4. The pharmaceutical composition of claim 1, wherein the modulation of exon skipping results in reducing the level of a transcription product and the first nucleic acid strand is capable of hybridizing to a non-coding region of a precursor mRNA inside of the cell.

5. The pharmaceutical composition of claim 1, wherein the total number of natural DNA nucleotides, modified DNA nucleotides, and nucleotide analogs in the first nucleic acid strand is from 10 to 35.

6. The pharmaceutical composition of claim 1, wherein the bridged nucleotides are independently selected from LNA, cEt-BNA, amideBNA (AmNA), and cMOE-BNA.

7. The pharmaceutical composition of claim 1, wherein the first nucleic acid strand comprises bridged nucleotides independently selected from a nucleotide in which the carbon atom at the 2'-position and the carbon atom at the 4'-position are bridged by 4'-$(CH_2)_p$—O-2',4'-$(CH_2)_p$—$CH_2$-2',4'-$(CH_2)_p$—S-2',4'-$(CH_2)_p$—OCO-2',4'-$(CH_2)_n$—N$(R_3)$—O—$(CH_2)_m$-2', where p, m and n represent an integer from 1 to 4, an integer from 0 to 2, and an integer from 1 to 3; respectively, and $R_3$ represents a hydrogen atom, an alkyl group, an alkenyl group, a cycloalkyl group, an aryl group, an aralkyl group, an acyl group, a sulfonyl group, a fluorescent or chemiluminescent label, a functional group with nucleic acid cleavage activity, or an intracellular or intranuclear localization signal peptide.

8. The pharmaceutical composition of claim 1, wherein at least one of the modified nucleotides or one of the nucleotide analogs in the first nucleic acid strand is phosphorothioated.

9. The pharmaceutical composition of claim 1, wherein the first nucleic acid strand and/or the second nucleic acid strand further comprises a functional moiety having a function selected from a labeling function, a purification function, and a targeted delivery function.

10. The pharmaceutical composition according to claim 9, wherein said functional moiety is a molecule selected from a lipid, a sugar, a peptide, and a protein.

11. The pharmaceutical composition according to claim 10, wherein the functional moiety is joined to the 3'-terminal nucleotide and/or the 5'-terminal nucleotide of the first or second nucleic acid strand, or a third nucleic acid strand.

12. The pharmaceutical composition according to claim 11, wherein the functional moiety is a peptide or protein selected from a receptor ligand and an antibody.

13. The pharmaceutical composition according to claim 12, wherein the functional moiety is independently selected from P007 and B peptide.

14. A method for modulating exon skipping of a coding or non-coding RNA in a mammalian cell comprising contacting the mammalian cell with the pharmaceutical composition of claim 1.

* * * * *